(12) United States Patent
Perez et al.

(10) Patent No.: US 8,795,731 B1
(45) Date of Patent: Aug. 5, 2014

(54) CERIUM OXIDE NANOPARTICLE-BASED DEVICE FOR THE DETECTION OF REACTIVE OXYGEN SPECIES AND MONITORING OF CHRONIC INFLAMMATION

(75) Inventors: Jesus Manuel Perez, Orlando, FL (US); Charalambos Kaittanis, Oviedo, FL (US); Atul Asati, Orlando, FL (US); Santimukul Santra, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 494 days.

(21) Appl. No.: 12/924,976

(22) Filed: Oct. 8, 2010

Related U.S. Application Data

(60) Provisional application No. 61/250,750, filed on Oct. 12, 2009.

(51) Int. Cl.
    *A61K 9/14* (2006.01)
(52) U.S. Cl.
    USPC ........................................................ 424/489
(58) Field of Classification Search
    CPC ............ A61K 33/00; A61K 47/48861; A61K 49/0043; A61K 49/0093
    See application file for complete search history.

(56) References Cited

U.S. PATENT DOCUMENTS

| | | | |
|---|---|---|---|
| 5,089,860 A | 2/1992 | Deppe et al. | |
| 5,411,647 A | 5/1995 | Johnson et al. | |
| 5,486,359 A | 1/1996 | Caplan et al. | |
| 5,910,311 A | 6/1999 | Boussourira | |
| 5,961,993 A | 10/1999 | Boussourira | |
| 6,042,714 A | 3/2000 | Lin et al. | |
| 6,103,247 A | 8/2000 | Boussourira | |
| 6,139,985 A | 10/2000 | Borglum et al. | |
| 6,316,012 B1 | 11/2001 | N'Guyen | |
| 6,327,074 B1 | 12/2001 | Bass et al. | |
| 6,368,577 B1 | 4/2002 | Kropf et al. | |
| 6,406,685 B1 | 6/2002 | Philippe | |
| 6,468,551 B1 | 10/2002 | Diec | |
| 6,497,863 B1 | 12/2002 | Wachter | |
| 6,497,865 B1 | 12/2002 | Griesbach | |
| 6,501,590 B2 | 12/2002 | Bass et al. | |
| 6,592,746 B1 | 7/2003 | Schmid-Schoenbein et al. | |
| 6,654,161 B2 | 11/2003 | Bass et al. | |
| 6,833,192 B1 * | 12/2004 | Caruso et al. | 428/403 |
| 6,844,387 B2 | 1/2005 | Bass et al. | |
| 6,890,896 B1 | 5/2005 | Shashoua | |
| 7,005,504 B2 | 2/2006 | Hsei et al. | |
| 7,075,707 B1 | 7/2006 | Rapaport et al. | |
| 7,141,227 B2 | 11/2006 | Chan | |
| 7,270,813 B2 | 9/2007 | Shimp et al. | |
| 7,347,987 B2 | 3/2008 | McGinnis et al. | |
| 7,431,758 B2 | 10/2008 | Ota et al. | |
| 7,442,686 B2 | 10/2008 | Lasko et al. | |
| 7,471,706 B2 | 12/2008 | Bass et al. | |
| 7,504,356 B1 | 3/2009 | Self et al. | |
| 7,507,480 B2 | 3/2009 | Sugaya | |
| 7,534,453 B1 | 5/2009 | Zigaliznski et al. | |
| 7,563,459 B2 | 7/2009 | Phillips et al. | |
| 7,642,250 B2 | 1/2010 | Williams | |
| 7,687,505 B2 | 3/2010 | Sugaya | |
| 7,718,261 B2 | 5/2010 | Katusic et al. | |
| 7,772,375 B2 | 8/2010 | Greferath et al. | |
| 7,888,119 B2 | 2/2011 | Sugaya et al. | |
| 7,899,093 B1 | 3/2011 | Bass et al. | |
| 7,906,147 B2 | 3/2011 | Hainfeld | |
| 7,914,617 B2 | 3/2011 | Yadav | |
| 8,080,420 B2 | 12/2011 | Sugaya | |
| 8,097,270 B2 | 1/2012 | Ketelson et al. | |
| 8,172,901 B2 | 5/2012 | Goulet et al. | |
| 2003/0050709 A1 | 3/2003 | Noth et al. | |
| 2003/0187077 A1 | 10/2003 | Chane-Ching | |

(Continued)

FOREIGN PATENT DOCUMENTS

| | | |
|---|---|---|
| WO | WO 99/15891 | 4/1999 |
| WO | WO 03/059263 A2 | 7/2003 |

(Continued)

OTHER PUBLICATIONS

Gomes et al, Fluorescence probes used for detection of reactive oxygen species, J. Biochem. Biophys. Methods, 2005, vol. 65, pp. 45-80.*

(Continued)

*Primary Examiner* — Michael G Hartley
*Assistant Examiner* — Sun Y Kim
(74) *Attorney, Agent, or Firm* — Brian S. Steinberger; Law Offices of Brian S. Steinberger, P.A.

(57) ABSTRACT

A polymer-coated cerium oxide based device and system is disclosed for detecting reactive oxygen species and monitoring chronic inflammation. The device and system encapsulate free therapeutic nanoparticle elements not present in a living body in a prosthetic or implantable unit. Embodiment one is a two-chamber structure with a reactive oxygen species (ROS) scavenging component on one end and at the opposite end is an imaging agent consisting of at least one of a fluorophore capable of fluorescence emission, a chemiluminescent agent, a magnetic relaxation agent and an X-ray contrast agent. Embodiment two is a single chamber device consisting of a multifunctional nanocomposite with a ROS-scavenging nanoparticle constituent (nanoceria) and a multimodal reporting nanoparticle component (i.e. Dex-IO-DiR). The device and system are utilized in treatment of diseases with a pro-inflammatory component, including, but not limited to, Crohn's disease, ulcerative colitis, inflammatory bowel disease, cystic fibrosis, arthritis, and cancer chemotherapy.

24 Claims, 28 Drawing Sheets

(56) References Cited

U.S. PATENT DOCUMENTS

| | | | |
|---|---|---|---|
| 2004/0062753 | A1 | 4/2004 | Rezania et al. |
| 2005/0159820 | A1 | 7/2005 | Yoshikawa et al. |
| 2005/0164377 | A1 | 7/2005 | Miyabayashi et al. |
| 2005/0171192 | A1 | 8/2005 | Gehlsen |
| 2006/0110440 | A1 | 5/2006 | Sugaya |
| 2006/0280729 | A1 | 12/2006 | Mistry |
| 2007/0003621 | A1 | 1/2007 | Nagia et al. |
| 2008/0248565 | A1* | 10/2008 | Katzen et al. ............ 435/325 |
| 2008/0274202 | A1* | 11/2008 | Kraig et al. ............. 424/491 |
| 2009/0087493 | A1 | 4/2009 | Dai et al. |
| 2009/0098574 | A1 | 4/2009 | Brisson et al. |
| 2010/0092384 | A1* | 4/2010 | Bumb et al. ............. 424/1.29 |
| 2010/0098768 | A1* | 4/2010 | Andreescu et al. ....... 424/489 |
| 2010/0151000 | A1 | 6/2010 | Thomas et al. |
| 2012/0107229 | A1* | 5/2012 | Huang et al. ............ 424/1.11 |

FOREIGN PATENT DOCUMENTS

| | | |
|---|---|---|
| WO | WO 2006/118954 | 11/2006 |
| WO | WO 2006/118954 A2 | 11/2006 |
| WO | WO 2006130473 A2 * | 12/2006 |
| WO | WO 2007/002662 | 1/2007 |
| WO | WO 2007/002662 A2 | 1/2007 |
| WO | WO 2008/064357 A2 | 5/2008 |
| WO | PCT/US2009/041675 | 6/2009 |
| WO | WO 2009/132277 A1 | 10/2009 |

OTHER PUBLICATIONS

Daniel et al, Multi-reservoir device for detecting a soluble cancer biomarker, Lap Chip, 2007, vol. 7, pp. 1288-1293.*

Trehin et al, Fluorescent Nanoparticle Uptake for Brain Tumor Visualization, Neoplasia, 2006, vol. 8, pp. 302-311.*

Fluorescent Dyes from life technologies, a subsidiary of Molecular Probes, Inc.*

Pittet et al, Labeling of immune cells for in vivo imaging using magnetofluorescent nanoparticles, Nature Protocols, 2006, vol. 1, pp. 73-79.*

Santra et al, Drug/Dye-Loaded, Multifunctional Iron Oxide nanoparticles for Combined Targeted Cancer Therapy and Dual Optical/Mr-Imaging, Small, 2009, vol. 5, pp. 1862-1868.*

Niu, et al., Cardioprotective effects of cerium oxide nanoparticles in a transgenic murine model of cardiomyopathy, Cardiovas. Res., 2006, pp. 549-559, vol. 73, No. 3.

Qureshi, et al. Increased exhaled nitric oxide following autologous peripheral hemotopietic stem-cell transplantation: a potential marker of idopathic pneumonia syndrome, Chest, 2004, pp. 281-287, vol. 125, No. 1.

Ohgushi, et al., Stem cell technology and bioceramics: from cell to gene engineering, J. Biomed. Mat. Res., 1999, pp. 913-927, vol. 48, abstract.

Dal Maschio, et al., Influence of Ce3+/Ce4+ ratio on phase stability and residual stress field in ceria-yttria stabilized zirconia plasma-sprayed coatings, J. Mat. Sci., 1992, pp. 5591-5596, vol. 27, abstract.

Ramsfjell, et al., Distinct requirements for optimal growth and in vitro expansion of human CD34+ CD38− bone marrow long-term culture-initiating cells (LTC-IC), extended LTC-IC, and murine in vivo long-term reconstituting stem cells, Blood, 1999, pp. 4093-4102, vol. 99, No. 12, abstract.

Devasenpathi, et al., Forming near net shape free-standing components by plasma spraying, Mat. Let., 2002, pp. 882-886, vol. 57.

Imamura, et al., Drusen, choroidal neovascularization, and retinal pigment epithelium dysfunction in SOD1-deficient mice: a model of age-related macular degeneration, PNAS, 2006, pp. 11282-11287, vol. 103, No. 30.

Hollyfield, et al., Oxidative damage-induced inflammation initiates age-related macular degeneration, Nature Medicine, 2008, pp. 194-198, vol. 14.

Birch, et al., Age-related macular degeneration: a target for nanotechnology derived medicines, International Journal of Nanomedicine, 2007, pp. 65-77, vol. 2, No. 1.

Maulik, N., Reactive oxygen species drives myocardial angiogenesis?, Antioxidants & Redox Signaling, 2006, pp. 2161-2168, vol. 8, Nos. 11-12.

McGinnis, et al. U.S. Appl. No. 12/772,523 Office Action mailed Sep. 15, 2011.

Ohia, et al., Pharmacological consequences of oxidative stress in ocular tissues, Mutation Research, 2005, pp. 22-36, vol. 579.

Liu, et al. Subtype lesions of neovascular age-related macular degeneration in Chinese patients, Braefe's Arch Clin Exp Opthalmol, 2007, pp. 1441-1445, vol. 245.

Silva, Seeing the benefits of ceria, Nature Nanotechnology, 2006, pp. 92-94, vol. 1.

Hahn, et al., Maculas affected by age-related macular degeneration contain increased chelatable iron in the retinal pigment epithelium and Bruch's membrane, Arch. Opthalmol., 2003, pp. 1099-1105, vol. 121.

Haywood, et al., Inflammation and angiogenesis in osteoarthritis, Arthritis & Rheumatism, 2003, pp. 2173-2177, vol. 48, No. 8.

Chen, et al., Rare earth nanoparticles prevent retinal degeneration induced by intracellular peroxides, Nature Nano Technology, 2006, pp. 142-148, vol. 1, No. 2, abstract.

Moongkarndi, et al, Antiproliferation, antioxidation and induction of apoptosis by Garcinia mangostana (mangosteen) on SKBR3 human breast cancer cell line, J. of Ethno-Pharmacology, 2004, pp. 161-166, vol. 90, abstract.

Margrain, et al., Do blue light filters confer protection against age-related macular degeneration?, Progress in Retinal and Eye Research, 2004, pp. 523-531, vol. 23, abstract.

Bailey, et al., Cerium oxide nanoparticles extend cell longevity and act as free radical scavengers, online, retrieved on Apr. 24, 2006, retrieved from http://www.med.miami.edu/mnbws/Rzigalinski11.html, abstract.

Tsai, The study of the synthesis of nano-grade cerium oxide powder, Materials Letters, 2004, pp. 2270-2274, vol. 58, abstract.

Rzigalinski, et al., Cerium oxide nanoparticles increase the lifespan of cultured brain cells and protect against free radical mechanical trauma, FASEB Journal, 2003, vol. 17, No. 4-5, page abstract No. 377.24, abstract.

Cook, et al., Neuronal damage induced by polychlorinated biphenyls is partially reversed by cerium oxide nanoparticles, online, 2003, retrieved from http://sfn.scholarone.com/itin2003/main.htm?new_page_id=126&abstract_id=14513&p_num=669.13&is_tech=0>, retrieved on Aug. 5, 2008, abstract.

Tsunekawa, S., et al., Lattice relaxation of monosize CeO2-x nanocrystalline particles, Applied Surface Science Elsevier Netherlands, 1999, pp. 53-56, vol. 152, No. 1-2, abstract.

Hooper, et al., New treatment in age-related macular degeneration, Clinical & Experimental Opthalmology, 2003, pp. 376-391, vol. 31, abstract.

Suzuki, et al., Preparation and characteristics of magnetite-labelled antibody with the use of poly(ethylene glycol) derivatives, Biotech. and Applied Biochem., 1995, pp. 335-345, vol. 21.

Dong, et al., Activation of glassy carbon electrodes by dispersed metal oxide particles, Dept. of Chemistry, OSU, downloaded 2011, pp. 813, abstract.

Shui, et al., Morphological observation on cell death and phagocytosis induced by ultraviolet irradiation in a cultured human lens epithelial cell line, Exp. Eye Res., 2000, pp. 608-619, vol. 71, No. 6, abstract.

Xijuan, et al., Size-dependent optical properties of nanocrystalline CeO2:Er obtained by combustion synthesis, Phys. Chem., 2001, pp. 5266-5269, vol. 3, abstract.

Guo, Green and red upconversion luminescence in CeO2:Er3+ powders produced by 785 nm laser, Journal of Solid State Chemistry, 2007, pp. 127-131, vol. 180, No. 1, abstract.

Perez, et al., Synthesis of biocompatible dextran-coated nanoceria with pH-Dependent antioxidant properties, Small, 2008, pp. 552-556, vol. 4, No. 5, abstract.

Pirmohamed, et al., Nanoceria exhibit redox state-dependent catalase mimetic activity, Chem. Comm, 2010, pp. 2736-2738, vol. 46, abstract.

(56) References Cited

OTHER PUBLICATIONS

Chen, et al., Rare earth nanoparticles prevent retinal degeneration induced by intracellular peroxides, Nature Publishing Group, 2006, pp. 1-9, abstract.

Karakoti, et al., Direct synthesis of nanoceria in aqueous polyhydroxyl solutions, J. Phys. Chem. C, 2007, pp. 17232-17240, vol. 111, No. 46, abstract.

Tarnuzzer, et al., Vacancy engineered ceria nanostructures for protection from radiation-induced cellular damage, Nano Lett, 2005, pp. 2573-2577, vol. 4, No. 12, abstract.

Heckert, et al., The role of cerium redox state in the SOD mimetic activity of nanoceria, Biomaterials, 2008, pp. 2705-2709, vol. 29, abstract.

Schubert, et al., Cerium and yttrium oxide nanoparticles are neuroprotective, Biochemical and Biophysical Research Communications, 2006, pp. 86-91, vol. 342.

Zhang, et al., Cerium oxide nanoparticles: size selective formation and structure analysis, Applied Physics Letters, 2002, pp. 127-129, vol. 81, No. 1.

Patil, et al., Surface-derived nanoceria with human carbonic anhydrase II inhibitors and flourphores: a potential drug delivery device, J. Phys. Chem. C., 2007, pp. 8437-8442, vol. 111, No. 24, abstract.

Patil, et al., Synthesis of nanocrystalline ceria particles for high temperature oxidation resistant coating, Journal of Nanoparticle Research, 2002, pp. 433-438, vol. 4, abstract.

Jin, et al., Nanopartical-mediated drug delivery and gene therapy, Biotechnol. Prog, 2007, pp. 32-41, vol. 23, abstract.

Eck, et al., PEGylated gold nanoparticles conjugated to monoclonal F19 antibodies as targeted labeling agents for human pancreatic carcinoma tissue, ACS Nano, 2008, pp. 2263-2272, vol. 2, No. 11, abstract.

Nafee, Dissertation entitled "Cationically-modified nanoparticles for the polmonary delivery of the telomerase inhibitor 2'-O-Methyl RNA for the treatment of lung cancer," Dissertation zur Erlangung des Grades des Doktors der, Naturwissenschaftern der Naturwissenschaftilch—Technischen Fakul't III Chemie, Pharmazie, Bio-und Werstoffwissenschaften der Universit des Saarlandes, 2008, abstract.

Nazem, et al., Nanotechnology for Alzheimer's disease detection and treatment, Insciences J., 2011, pp. 169-193, vol. 1, No. 4, abstract.

Olivier, et al., Synthesis of pegylated immunonanoparticles, Pharmaceutical Research, 2002, pp. 1137-1143, vol. 19, No. 8, abstract.

Otsuka, et al., PEGylated nanoparticles for biological and pharmaceutical applications, Advanced Drug Delivery Reviews, 2003, pp. 403-419, vol. 55, abstract.

Qi, et al. Redispersible hybrid nanopowders; cerium oxide nanoparticle complexes with Phosphonated-PEG pligomers, ACS Nano, 2008, pp. 879-888, vol. 2, No. 5, abstract.

Sokolov, et al., Real-time vital optical imaging of precancer using anti-epidermal growth factor receptor antibodies conjugated to gold nanoparticles, Cancer Res. 2003, vol. 63, abstract. (Title Only).

Suh, et al., Multifunctional nanosystems at the interface of physical and life sciences, Physicaplus, 2010, issue 13, abstract.

PCT/US2011/0044329, PCT International Search Report and the Written Opinion of the International Searching Authority, cover page.

Buettner, et al., Ascorbate (Vitamin C) its antioxidant chemistry, Free Radical and Radiation Biology Program, Dept. of Radiation Oncology, University of Iowa, 1 page.

Chen, et al., Rare Earth Nanoparticles Prevent Retinal Degeneration Induced by Intracellular Peroxides, Nature's Publishing Group, 2006, pp. 142-150, vol. 1.

Tarnuzzer, et al., Vacancy Engineered Ceria Nanostructures for Protection from Radiation-Induced Cellular Damage, American Chemical Society, 2005, pp. 2573-2577, vol. 5, No. 12.

Rzigalinksi, Nanoparticles and Cell Longevity, Technology in Cancer Research & Treatment, 2005, pp. 651-659, vol. 4, No. 6.

Shacter, et al., Oxidative Stress Interferes with Cancer Chemotherapy: Inhibition of Lymphoma Cell Apoptosis and Phagocytosis, Blood, 2000, pp. 307-313, vol. 96, No. 1.

Chung, et al., Molecular Inflammation: Underpinnings of Aging and Age-Related Diseases, Ageing Research Reviews, 2009, pp. 18-30, vol. 8.

Asati, et al., Oxidase-Like Activity of Polymer-Coated Cerium Oxide Nanoparticles, Angewandte Chemie, 2009, pp. 2308-2312, vol. 48.

Xia, et al., Comparison of the Mechanism of Toxicity of Zinc Oxide and Cerium Oxide Nanoparticles Based on Dissolution and Oxidative Stress Properties, American Chemical Society, 2008, pp. 2121-2134, vol. 2, No. 10.

Tan, et al., An Efficient Method for Dephosphorylation of Phosphopeptides by Cerium Oxide, J. Mass Spectrom., 2008, pp. 628-632, vol. 43.

Perez, et al., Synthesis of Biocompatible Dextran-Coated Nanoceria with pH-Dependent Antioxidant Properties, Wiley InterScience, 2008, pp. 552-556, vol. 4, No. 5.

Das, et al., Auto-Catalytic Ceria Nanoparticles Offer Neuroprotection to Adult Rat Spinal Cord Neurons, ScienceDirect Biomaterials, 2007, pp. 1918-1925, vol. 28.

Niu, et al., Cardioprotective Effects of Cerium Oxide Nanoparticles in a Transgenic Murine Model of Cardiomyopathy, Cardiovascular Research, 2007, pp. 549-559, vol. 73.

\* cited by examiner

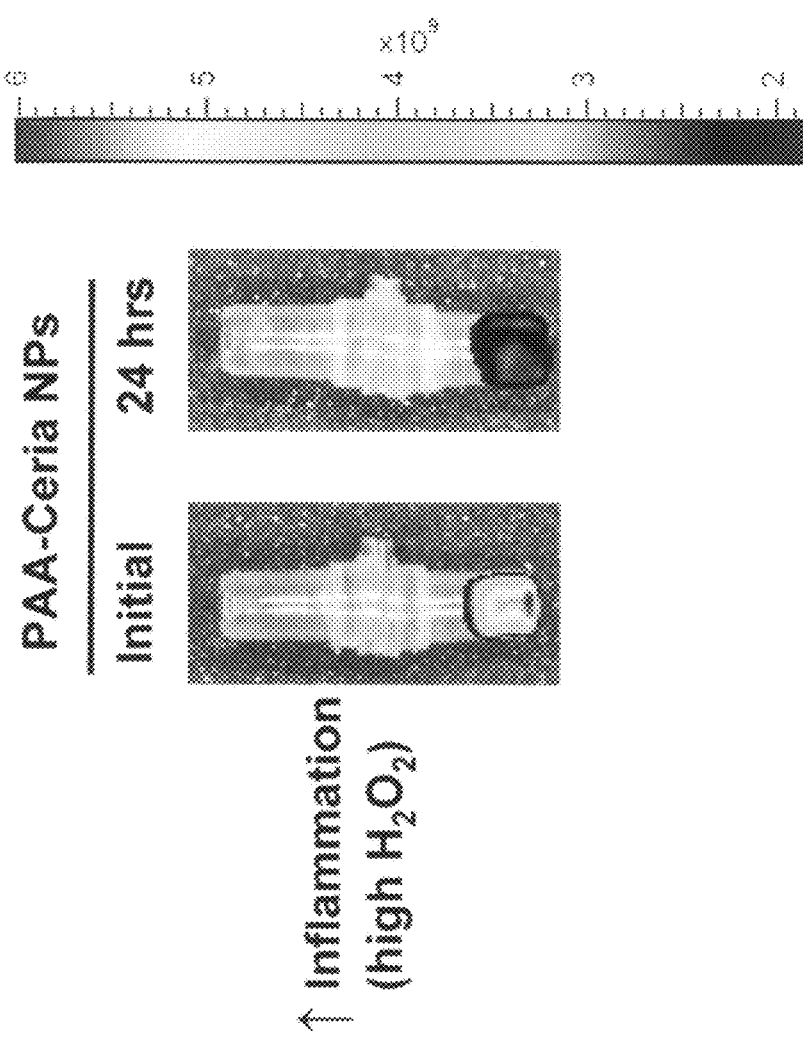

| | Ce$^{+3}$ | Ce$^{+4}$ |
|---|---|---|
| PAA-Ce (pH 7) | 57 % | 43 % |
| PAA-Ce (pH 4) | 61 % | 39 % |
| PAA-Ce (pH 7, 1 μM H$_2$O$_2$) | 58 % | 42 % |
| PAA-Ce (pH 4, 1 μM H$_2$O$_2$) | 44 % | 56 % |
| PAA-Ce (pH 7, 6 μM H$_2$O$_2$) | 39 % | 61 % |

Figure 14

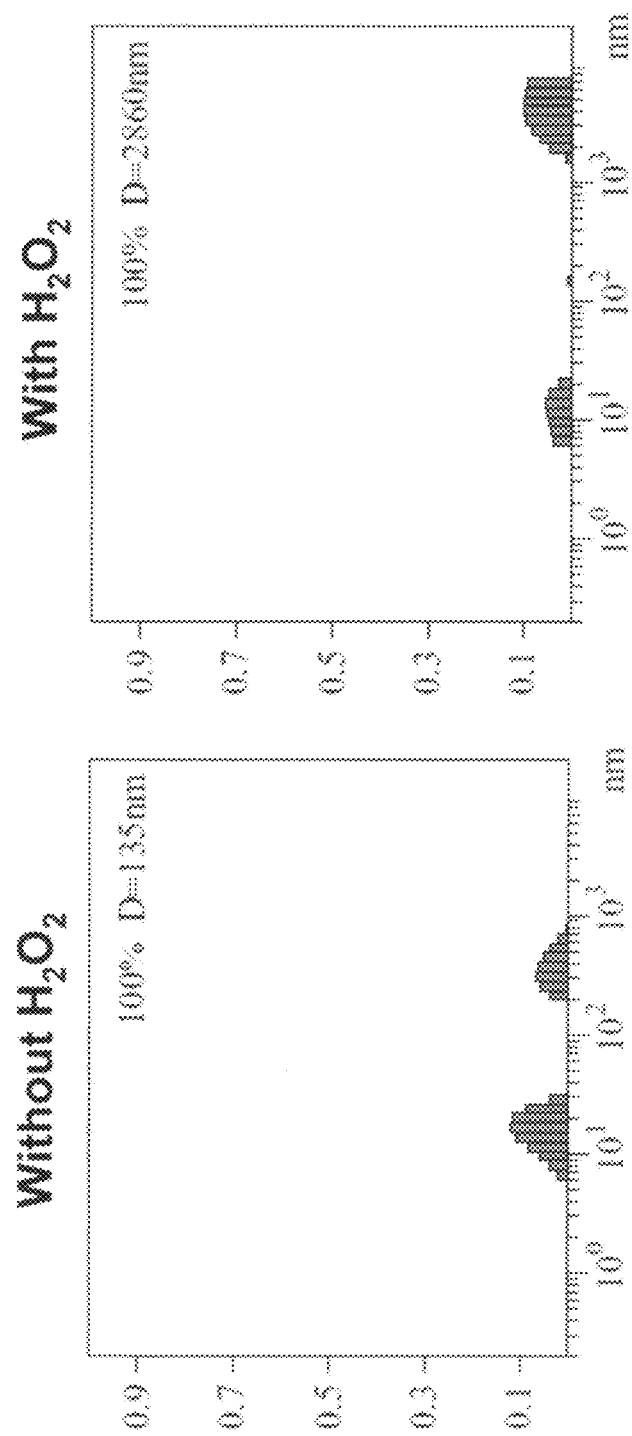
Figure 17A  Without H₂O₂
Figure 17B  With H₂O₂

1. Control; 2. 1 µM $H_2O_2$; 3. 6 µM $H_2O_2$; 4. 6 µM $H_2O_2$ (pH 4.0)

5- Control; 6- 1 μM $H_2O_2$; 7- 6 μM $H_2O_2$; 8- 6 μM $H_2O_2$ (pH 4.0)

CERIUM OXIDE NANOPARTICLE-BASED DEVICE FOR THE DETECTION OF REACTIVE OXYGEN SPECIES AND MONITORING OF CHRONIC INFLAMMATION

RELATED APPLICATIONS

This invention claims the benefit of priority from U.S. Provisional Patent Application Ser. No. 61/250,750 filed on Oct. 12, 2009, which is incorporated by reference.

GOVERNMENT LICENSE RIGHTS

This invention was made with Government support under Agency contract number K01 CA101781 and R01 GM084331 awarded by the National Institutes of Health. The government has certain rights in this invention.

FIELD OF THE INVENTION

This invention relates to uses of nanoceria particles, and in particular to nanoceria-based methods, systems and devices useful in detecting reactive oxygen species and monitoring chronic inflammation in vivo.

BACKGROUND AND PRIOR ART

Most recently, it has been found that nanosized cerium oxide (nanoceria) possesses antioxidant activity at physiological pH and has potential use in biomedical applications, such as protection against radiation damage, oxidative stress and inflammation, as reported by various researchers, including R. W. Tarnuzzer, et al. in *Nano Lett* 2005, 5, 2573; J. P. Chen, et al. in *Nature Nanotechnology* 2006, 1, 142; J. Niu, et al in *Cardiovasc Res* 2007, 73, 549; M. Das, et al. in *Biomaterials* 2007, 28, 1918 and J. M. Perez, et al. in *Small* 2008.

Biological systems have evolved to utilize readily available elements, such as carbon, oxygen, hydrogen, nitrogen, calcium and iron. Less abundant elements may be utilized as co-factors in enzymatic complex factors, or can be found in chelated forms surrounded by aromatic rings and coordinated bonding. However, many elements, including rare earths, such as cerium, are not present in living organisms, due to their highly reactive nature resulting in toxicity.

Hence, cells do not have protective apparatuses against elements not present in living organisms, and organisms do not have mechanisms to handle the storage, utilization and release of these elements from the body. For instance, lead and arsenic accumulate in the body and can lead to severe pathological conditions, including organ failure and death. Also, nanoparticles composed of metals such as cadmium in Quantum dots (QDOTS) are partially toxic.

Similarly, cerium oxide nanoparticles, despite being potent reactive oxygen species (ROS) scavengers and selective cytoprotective agents, have shown cellular uptake and intracellular residency of cerium oxide nanoparticles which induces dephosphorylation of various substrates, causing aberrant cell signaling and alterations in the transcriptional and post-translational levels, as reported by J. M. Perez et al. in "Synthesis of biocompatible dextran-coated nanoceria with pH-dependent antioxidant properties" *Small*, 2008. 4(5): 552-556, Tan, F., et al. in "An efficient method for dephosphorylation of phosphopeptides by cerium oxide" *J Mass Spectrom*, 2008. 43(5): 628-632 and Xia, T., et al. in "Comparison of the mechanism of toxicity of zinc oxide and cerium oxide nanoparticles based on dissolution and oxidative stress properties" *ACS Nano*, 2008. 2(10): 2121-2134.

Furthermore, Asati, A., et al. in "Oxidase-Like Activity of Polymer-Coated Cerium Oxide Nanoparticles" *Angew Chem Int Ed Engl*, 2009 reported the oxidase-like activity of these nanoparticles in acidic microenvironments, which may facilitate the oxidation of intracellular and extracellular components. Most importantly, as cerium is not found in the human body and there are no clearance mechanisms for it, cerium may cause toxicity, contrary to iron oxide nanoparticles, where the iron-containing core can be metabolized and uptaken by ferritin and transferrin, as reported by Xia, T., et al. in "Comparison of the mechanism of toxicity of zinc oxide and cerium oxide nanoparticles based on dissolution and oxidative stress properties" *ACS Nano*, 2008, supra and Rzigalinski, B. A., "Nanoparticles and cell longevity" *Technol Cancer Res Treat*, 2005 4(6): 651-659.

In view of the above findings, potential in vivo application of these nanoparticles has been limited. The prior art in the applications of nanoceria pertains to the administration and use of the nanoparticles free in solution, hence nanoparticle clearance and toxicity may be observed. No prior art reports the encasing of these nanoparticles in a device, such as described in the present invention, thereby preventing direct exposure of the living organism to these nanoparticles.

Thus, a device encapsulating therapeutic elements not present in a living body, such as cerium oxide, is an attractive alternative, preventing the adverse side effects from free nanoparticles in circulation. Therefore, for these reasons, it would be advantageous to introduce nanoparticles within devices to minimize their exposure, accumulation and potential toxicity to biological systems. Such an embodiment would be classified as a prosthetic (implantable) device and not a drug, expediting the adoption of these nanoparticles in therapy and the clinic.

It is desirable to extend the utility of the coated nanoceria particles as a stable, effective, therapeutic device, system or method for detecting reactive oxygen species and monitoring chronic inflammation in biological tissue, while causing no adverse side effects or toxicity to the body. The present invention provides a much needed weapon in the arsenal for treating a broad range of ailments with a pro-inflammatory component, for cancer therapy, for patients with transplants or prosthetic devices and the like.

SUMMARY OF THE INVENTION

A primary objective of the present invention is to provide a device, system and method encapsulating therapeutic elements not present in a living body, such as cerium oxide nanoparticles, in a prosthetic or implantable unit thereby preventing adverse side effects from free nanoparticles in circulation.

A secondary objective of the present invention is to provide a cerium oxide nanoparticle-based device, system and method for the detection of reactive oxygen species (ROS).

A third objective of the present invention is to provide a cerium oxide nanoparticle-based system, method and device for monitoring chronic inflammation.

A fourth objective of the present invention is to provide a cerium oxide nanoparticle-based system, method and device for the detection of reactive oxygen species (ROS) and monitoring of chronic inflammation, through the co-encasing of cerium oxide and fluorescent polymeric iron oxide nanoparticles (including Dex-IO-DiR and PAA-IO-DiI) in a two-chamber biocompatible device utilizing the potent ROS scavenging activity of cerium oxide nanoparticles.

A fifth objective of the present invention is to provide a cerium oxide nanoparticle-based system, method and device for the detection of reactive oxygen species (ROS) and monitoring of chronic inflammation, through the interspersing of cerium oxide and fluorescent polymeric iron oxide nanoparticles (including Dex-IO-DiR and PAA-IO-DiI) in a single chamber biocompatible device utilizing the potent ROS scavenging activity of cerium oxide nanoparticles.

A sixth objective of the present invention is to provide a stable, effective, cerium oxide nanoparticle-based therapeutic device, system and method for detecting reactive oxygen species and monitoring chronic inflammation in biological tissue, while causing no adverse side effects or toxicity to the body.

A seventh objective of the present invention is to provide monitoring of inflammation levels by changes in fluorescence emission (increase or decrease in the signal measured via optical methods), changes in magnetic relaxation (increase or decrease in the signal assessed via MRI), or alterations in other modalities' properties such as, X-ray contrast).

A preferred device of the present invention encapsulates free therapeutic nanoparticle elements not present in a living body in a prosthetic or implantable unit having a first chamber for a reactive oxygen species (ROS) scavenging component having an exterior semi-permeable membrane surface and an interior cavity containing the ROS scavenging component, a second chamber for an imaging agent having an exterior semi-permeable membrane surface and interior cavity containing the imaging agent, and the first chamber and the second chamber joined in a non-communicating manner so that both the first chamber and the second chamber independently communicate with an aqueous environment through the exterior semi-permeable membrane of each chamber allowing the diffusion of ROS from the environment on the exterior of the first chamber and the exterior of the second chamber such that the device can sense elevated non-physiological reactive oxygen species (ROS) levels associated with at least one of the following conditions, inflammation, exposure to radiation, and changes in a tissue/cellular micro-environment.

In the preferred device, the ROS-scavenging component in the first chamber is a plurality of nanoparticles selected from at least one of a polymer-coated cerium oxide that is coated with at least one of dextran and polyacrylic acid, and polymeric nanoparticles encapsulating a "soft" ROS-scavenging agent, selected from at least one of polymeric nanoparticles encapsulating proteins, polymeric nanoparticles encapsulating chemicals and polymeric nanoparticles encapsulating a small molecule.

It is preferred that the protein encapsulated by polymeric nanoparticles is selected from at least one of catalase, superoxide dismutase and the chemical encapsulated by polymeric nanoparticles is peroxidase and the small molecule encapsulated by polymeric nanoparticles is reduced glutathione.

In the preferred device, the second chamber contains an imaging agent selected from at least one of a fluorophore capable of fluorescence emission, a chemiluminescent agent, a magnetic relaxation agent and an X-ray contrast agent encapsulated within a plurality of polymeric cavities in a polymer-coated nanoparticle selected from at least one of iron oxide, bismuth, europium, gadolinium and chelates thereof, coated with dextran, PAA, HBPE, PLGA, and mixtures thereof.

The preferred imaging agent is a hydrophobic fluorophore selected from at least one of octodecyl indocarbocyanine (DiI), indodicarbocyanine (DiD) and indotricarbocyanine (DiR) encapsulated within the plurality of polymeric cavities of the polymer-coated nanoparticle selected from at least one of iron oxide, bismuth, europium, gadolinium and chelates thereof, coated with dextran, PAA, HBPE, PLGA, and mixtures thereof.

It is also preferred that the imaging agent in the second chamber is a hydrophilic fluorophore selected from at least one of cyanine 5.5 (Cy5.5) and ICG encapsulated within the plurality of polymeric cavities of the polymer-coated nanoparticle of iron oxide, bismuth, europium, gadolinium and chelates thereof, coated with dextran, PAA, HBPE, PLGA, and mixtures thereof.

It is further preferred that the polymer-coated nanoparticles of iron oxide are coated with polymers selected from dextran and polyacrylic acid that are used to monitor reactive oxygen species generation through magnetic resonance imaging (MRI). The polymer-coated nanoparticles of iron oxide are also used to monitor inflammation and upregulated reactive oxygen species (ROS) production through fluorescence-based optical methods.

The reactive oxygen species (ROS) scavenging component of the preferred device protects the imaging agent from exposure to ultraviolet (UV) radiation.

A second embodiment of a preferred device encapsulates free therapeutic nanoparticle elements not present in a living body in a prosthetic or implantable unit having a single chamber containing a reactive oxygen species (ROS) scavenging component interspersed with an imaging agent in a preselected ratio of 1:1, 1:2 and 2:1, whereby the scavenging component and the imaging component simultaneously communicate with an aqueous environment through the exterior semi-permeable membrane of the single chamber allowing the diffusion of ROS from the environment on the exterior of the chamber such that the device can sense elevated non-physiological reactive oxygen species (ROS) levels associated with at least one of the following conditions, inflammation, exposure to radiation and changes in a cellular micro-environment; thereby forming a single chamber device consisting of a nanocomposite, derived from the conjugation and linking of polymer-coated nanoceria with at least one of the following nanoparticles, Dex-IO-DiR, PAA-IO-DiR and mixtures thereof.

It is preferred that the ROS scavenging component in the single chamber is a plurality of nanoparticles selected from a polymer-coated cerium oxide coated with at least one of dextran and polyacrylic acid, and polymeric nanoparticles encapsulating a "soft" ROS-scavenging agent, selected from at least one of polymeric nanoparticles encapsulating proteins, polymeric nanoparticles encapsulating chemicals and polymeric nanoparticles encapsulating a small molecule.

It is also preferred that the protein encapsulated by polymeric nanoparticles is selected from at least one of catalase, superoxide dismutase and the chemical encapsulated by polymeric nanoparticles is peroxidase and the small molecule encapsulated by polymeric nanoparticles is reduced glutathione.

The preferred imaging agent in the single chamber is selected from a fluorophore capable of fluorescence emission, a chemiluminescent agent, a magnetic relaxation agent and an X-ray contrast agent encapsulated within a plurality of polymeric cavities in a polymer-coated nanoparticle selected from at least one of iron oxide, bismuth, gadolinium, chelates of gadolinium and europium.

The imaging agent is a hydrophobic fluorophore selected from at least one of octodecyl indocarbocyanine(DiI), indodicarbocyanine (DiD) and indotricarbocyanine (DiR) encapsulated within the plurality of polymeric cavities of the polymer-coated nanoparticle selected from at least one of iron oxide, bismuth, gadolinium, chelates of gadolinium and europium.

It is most preferred that the imaging agent in the single chamber is a hydrophilic fluorophore selected from at least one of cyanine 5.5 (Cy5.5) and indocyanine green (ICG) encapsulated within the plurality of polymeric cavities of the polymer-coated nanoparticle of iron oxide, europium, bismuth, gadolinium, chelates of gadolinium, and mixtures thereof.

The polymer-coated nanoparticles of iron oxide are coated with polymers selected from dextran and polyacrylic acid are used to monitor reactive oxygen species generation through magnetic resonance imaging (MRI) and are also used to monitor inflammation and upregulated reactive oxygen species (ROS) production through fluorescence-based optical methods.

The reactive oxygen species (ROS) scavenging component of the single chamber device protects the imaging agent from exposure to ultraviolet (UV) radiation.

A preferred nanocomposite system encapsulating free therapeutic nanoparticle elements not present in a living body requires the preparation of a miniature device containing a reactive oxygen species (ROS) scavenging agent and a fluorophore imaging agent, implanting the miniature device in a physiological environment, exposing the miniature device to non-physiological ROS levels, and monitoring the near-infrared fluorophore changes and magnetic relaxation time shifts, signaling the abnormal ROS concentration.

The preferred nanocomposite system further consisting of a miniature device, that is exposed to elevated ROS levels and prevents the regeneration of the ROS scavenger, leading to multimodal sensing changes in fluorescence emission and an increase in the magnetic relaxation (MRI) times of the nanocomposite.

The preferred nanocomposite system further comprising multimodal tracking, having as components nanoparticles with chemiluminescence, magnetic relaxation or X-ray contrast agents.

The preferred nanocomposite system is transplantable as a distinct entity or part of a prosthetic device and is utilized in diseases with a pro-inflammatory component selected from the group consisting of, Crohn's disease, ulcerative colitis, inflammatory bowel disease, cystic fibrosis, and arthritis.

The nanocomposite system has a miniature device that is also utilized in a treatment regime monitoring the potential induction of inflammation in at least one of cancer chemotherapy and antimicrobial therapy and also in real-time monitoring of ROS during the synthesis of ROS-sensitive compounds.

The preferred nanocomposite system is also used in tissue protection against elevated ROS levels, in chemotherapy, prosthesis, and post-transplant operations.

Further objects and advantages of the present invention will be apparent from the following detailed description of a presently preferred embodiment, which is illustrated schematically in the accompanying drawings.

BRIEF DESCRIPTION OF THE FIGURES

FIG. 10B shows that a cerium oxide nanoparticle-based device with polymer-coated, polyacrylic acid (PAA), nanoceria does not protect the fluorescence emission of the DiI-Dex-IO nanoparticles from ROS for a period of 24 hours during inflammatory conditions and the presence of $H_2O_2$, allowing imaging of ROS generation.

FIG. 14 is a chart showing the regeneration capacity of polymer-coated, polyacrylic acid (PAA), nanoceria at pH 7; at pH 7 and 1.0 µM $H_2O_2$; at pH 4 and 1.0 µM $H_2O_2$; and at pH 7 and 6.0 µM H$_2$O$_2$; at low pH or high inflammation the nanoceria component cannot regenerate after exposure to reactive oxygen species (ROS).

FIG. 17A shows the clustering that is observed in the multimodal DiR-Dex-IO nanoparticles upon incubation without ROS, i.e., H$_2$O$_2$.

FIG. 17B shows the clustering that is observed in the multimodal DiR-Dex-IO nanoparticles upon incubation with ROS, i.e., H$_2$O$_2$.

DESCRIPTION OF THE PREFERRED EMBODIMENTS

Figure 1:
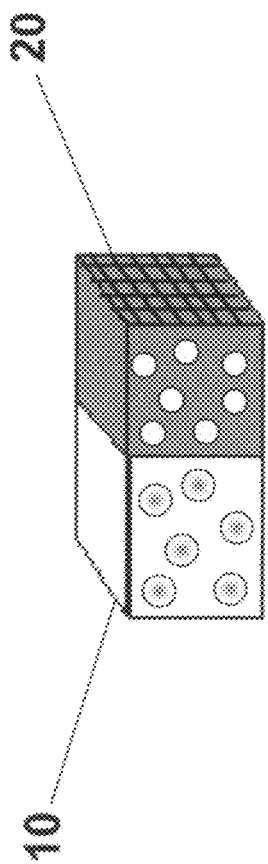
FIG. 1 is a conceptual diagram of the in vivo inflammation monitoring device of the present invention having two non-communicating chambers.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

Chemical names for fluorophores:
DiI-1,1'-dioctadecyl-3,3,3',3'-tetramethylindocarbocyanine perchlorate
DiD-1,1'-dioctadecyl-3,3,3',3'-tetramethylindodicarbocyanine perchlorate
DiR-1,1'-dioctadecyl-3,3,3',3'-tetramethylindotricarbocyanine iodide
ICG—indocyanine green (1H-Benz[e]indolium, 2-[7-[1, 1-dimethyl-3-(4-sulfobutyl)benz[e]indolin-2-ylidene]-1,3, 5-heptatrienyl]-1,1-dimethyl-3-(4-sulfobutyl)-, hydroxide)
Cy5.5-cyanine 5.5
Dex-IO-DiR is an abbreviation used herein to mean dextran-coated iron oxide with indotricarbocyanine (DiR) encapsulated in the polymeric dextran coating.
GSNO is an acronym for N—(N-L-y-glutamyl-5-nitroso-L-cysteinyl)-glycine
HBPE-DiI is an abbreviation used herein to mean hyperbranched polyester nanoparticles encapsulating indocarbocyanine (DiI).
MRI is an acronym for magnetic resonance imaging.
PAA is the acronym used herein to mean polyacrylic acid.
PAA-IO-DiI is an abbreviation used herein to mean polyacrylic acid-coated iron oxide nanoparticles encapsulating indocarbocyanine (DiI).
PLGA is the acronym used herein to mean Poly-Lactic-Co-Glycolic Acid.
"Physiological" is a term used herein to mean a characteristic of or appropriate to an organism's healthy or normal functioning which is measured by such factors as pH value, inflammation levels and the like. For example, the normal pH range of the intracellular fluid of cells is 6.9-7.4. One of the most important processes in the human body is the process by which the pH balance is maintained. Body pH measures the number of hydrogen ions in solution within the body. The pH scale ranges from 0-14 with <6.4 acidic and >6.4 alkaline for body fluid, not including blood which is a normal 7.3 pH. An acidic pH has a low ability to attract hydrogen ions, while an alkaline solution has a high ability to attract hydrogen ions. "p" stands for potential and "H" stands for hydrogen; henceforth, the potential of the body to attract hydrogen ions to secure balance and health.

ROS is an acronym for reactive oxygen species and for the research purposes herein hydrogen peroxide (H$_2$O$_2$) is used as a representative ROS chemical reagent.

The term "nanoceria" is used interchangeably with "cerium oxide nanoparticles" and is used to refer to the cerium oxide particles of multiple valences (Ce$^{+3}$/Ce$^{+4}$).

The present invention is capable of several embodiments which include a reactive oxygen species (ROS) scavenging agent, an imaging agent and multiple methods for the conjugation of the scavenging agent and imaging agent in a nano-composite device, as discussed in more detail below.

ROS Scavenging Agent:

The ROS scavenging agent used in the device consists of polymer-coated cerium oxide nanoparticles which have high antioxidant/free radical scavenging activity. The nanoparticles can be prepared using different synthetic protocols, including water-based formulations. At normal pH 7 nanoceria can effectively sequester ROS generated from various sources, including UV radiation, inflammation and chemical decomposition, as occurs with H$_2$O$_2$ and GSNO (S-nitroso-L-glutathione), due to the reversible switch from Ce$^{+3}$ and Ce$^{+4}$ states. This property renders cerium oxide an ideal ROS-scavenging agent. Moreover, at non-physiological pH or likely under conditions of enhanced ROS generation, nanoceria is not able to perform the autocatalytic reversible switching between its two valence states. This allows nanoceria to serve as a binary switch (ON/OFF) for aberrant ROS production. Apart from nanoceria, other ROS scavenging agents can be used, including "soft" ROS scavenging agents such as polymeric nanoparticles encapsulating proteins or chemicals, including, but not limited to, catalase, superoxide dismutase, peroxidase, and glutathione. "Soft" is used herein to mean non-metallic. Examples of "soft" or non-metallic ROC agents include, but are not limited to, polymeric nanoparticles encapsulating proteins, polymeric nanoparticles encapsulating chemicals such as, catalase, superoxide dismutase, peroxidase and small molecules, such as, reduced glutathione.

Imaging Agent:

The imaging agent consists of multimodal polymer-coated iron oxide nanoparticles, due to the nanoparticles' enhanced magnetic properties and FDA approval as clinical imaging agents for MRI. The polymer-coated iron oxide nanoparticles can be synthesized using diverse protocols, including the water-based alkaline precipitation method. Effective doping of the nanoparticles with a fluorophore can be achieved via different methodologies, such as the water diffusion procedure or via direct chemical conjugation. Apart from iron oxide nanoparticles, nanoparticles with gadolinium/gadolinium chelates, bismuth, Qdots, and europium can be used. A fluorophore, a conductive polymer or a fluorophore-polymer conjugate that is sensitive to ROS can serve as an imaging agent of ROS. Furthermore, imaging of ROS can be achieved via changes in the relaxation times of the nanoparticle solution (in the case of iron oxide T2).

Multimodal Nanocomposite:

The multifunctional and multimodal nanocomposite can be created by the conjugation of a ROS sensing nanoparticle formulation with an imaging nanoparticle preparation. Efficient nanocomposite formation can be achieved using various chemistries, including carbodiimide for aminated and carboxylated nanoparticles, or "click" chemistry for azide-propargylated nanoparticles. Hence for instance, the nanocomposite can be obtained by the "click" conjugation of propargylated PAA-coated nanoceria and azide-carrying DiR-PAA-IO, or carbodiimide conjugation of PAA-coated nanoceria and aminated DiR-Dex-10. Overall though, either constituent of the nanocomposite can be of "soft" or "hard" nanoparticles. Specifically, "soft" pertains to polymeric nanoparticles encapsulating a ROS scavenging agent of non-metallic nature (i.e. small molecule, protein) or an imaging agent entrapped within polymeric microdomains and cavities (i.e. fluorophore, chelated ions). On the other hand, "hard" nanoparticles include metallic nanoparticles, such as the ROS sensing polymer-coated nanoceria, polymer-coated iron oxide, and Quantum dots.

In the present invention, the cerium oxide nanoparticles or nanoceria are used in a biocompatible device for the detection of reactive oxygen species (ROS) and monitoring of chronic inflammation through the co-encasing of cerium oxide and fluorescent polymeric iron oxide nanoparticles, in an exemplary embodiment. Nanoparticle sizes are provided as an example, not for limitation of the invention. PAA-coated nanoceria can have particles that are approximately 6-8 nanometers (nm) in diameter; Dextran-coated nanoceria has particles that are approximately 10-14 nm in diameter; PAA-coated iron oxide nanoparticles are approximately 70-100 nm in diameter; Dextran-coated iron oxide nanoparticles (spherical) are approximately 60-120 nm in diameter; HBPE nanoparticles are approximately 100-130 nm in diameter.

Apart from a near-infrared fluorophore that can achieve deep tissue imaging by circumventing auto-fluorescence in mammalian tissue, iron oxide nanoparticles were used for magnetic resonance imaging (MRI) with better spatial resolution and deeper penetration. Results indicate that the device exhibits near-infrared fluorescence emission, under physiological or transient inflammatory conditions with low ROS concentrations. However, under prolonged exposure to ROS, simulating chronic inflammation, or in acidic and ROS-rich microenvironments fluorescence decreases significantly, due to the catalytic inactivation of cerium oxide nanoparticles and the fluorophore's susceptibility to ROS. Furthermore, we show that under elevated ROS, the iron oxide nanoparticles yield high T2 (spin-spin) relaxation times, which can be used as clinically applicable MRI tags for inflammation imaging.

FIG. 1 is a conceptual diagram of an in vivo inflammation monitoring device having a first chamber 10 contains antioxidant nanoparticles, such as nanoceria that functions as the reactive oxygen scavenging/sensing (ROS) chamber which is joined to a second chamber 20 contains nanoparticles that are fluorescent, magnetic or multimodal and is known herein as the monitoring chamber. Thus, construction of the inflammation monitoring device has two components; a first component consisting of a nanoparticle or a nanocomposite with cerium oxide, a ROS-sensitive/scavenging probe, and second component consisting of imaging agents, fabricated through the utilization of material synthesis techniques and conjugation chemistry approaches.

Figure 2:
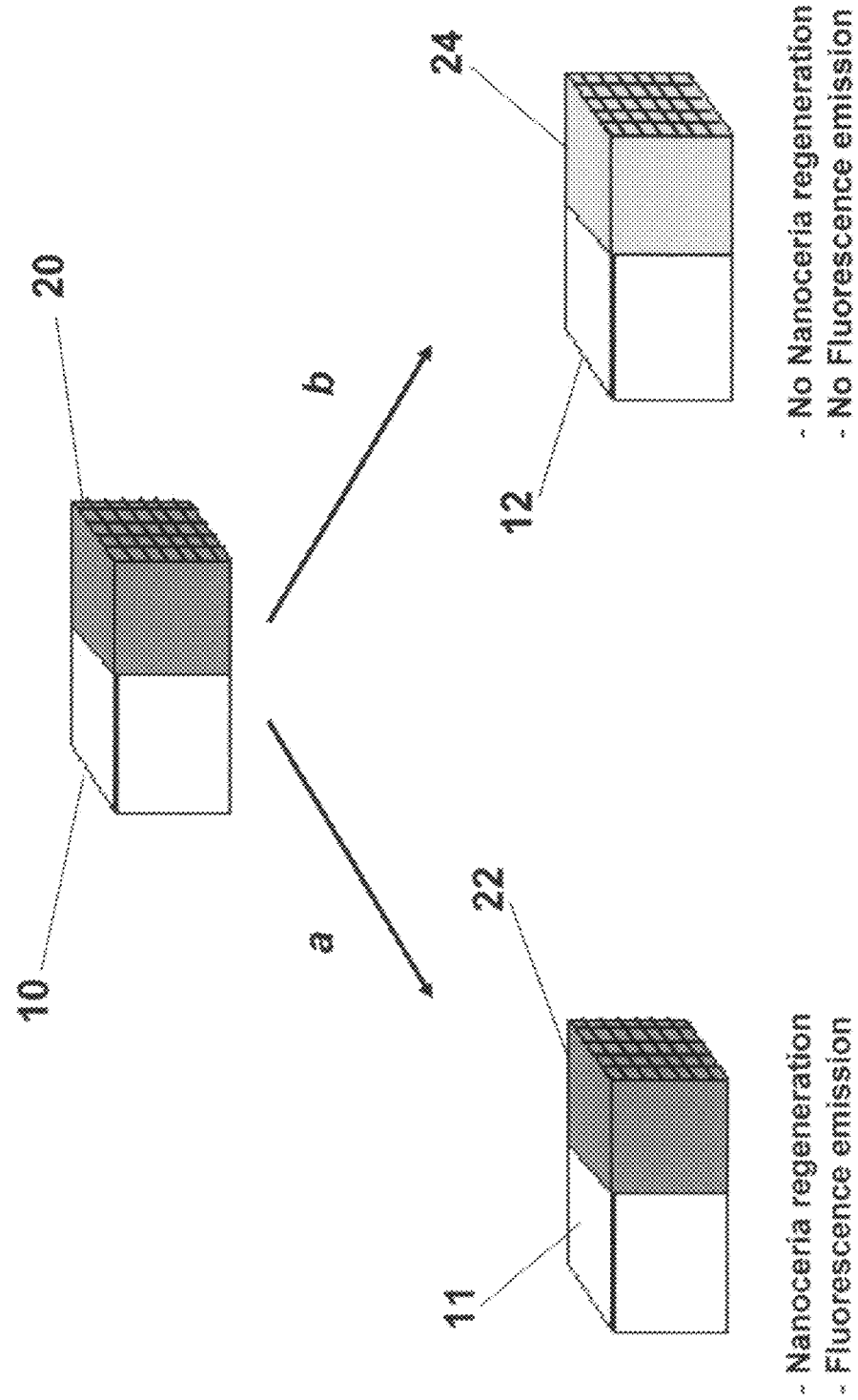
FIG. 2 is a schematic representation of the operation principle of the in vivo inflammation monitoring device of the present invention.

FIG. 2 is a schematic representation of the monitoring device's operating principle. The device consists of polymer-coated cerium oxide nanoparticles in a first chamber 10 and fluorophore-containing nanoparticles in a second chamber 20. The latter nanoparticles can be either fluorescent polymeric (i.e. hyperbranched polyester—HBPE-DiI) or polymer-coated iron oxide nanoparticles (i.e. DiR-Dextran-IO). Each one of the device's chambers independently communicates with the aqueous environment through a semi-permeable membrane, freely allowing the diffusion of ROS from the exterior to the device's chambers. Note that there is no communication between the two chambers. No communication means there is not any exchange of particles between the two chambers that are held in position by an adhesive or glue.

Under conditions of no or mild inflammation a, the device's cerium oxide nanoparticle component (nanoceria) in chamber 11 scavenges the generated ROS, as ROS production is either or transient, leading to preservation of the device's fluorescence emission in chamber 22. However, under conditions of chronic persistent inflammation b, nanoceria in chamber 12 does not have the ability to regenerate quickly enough, thus the excess ROS dim or switch off the device's fluorescence emission in chamber 24, due to the fluorophore's sensitivity to ROS.

Figure 3:
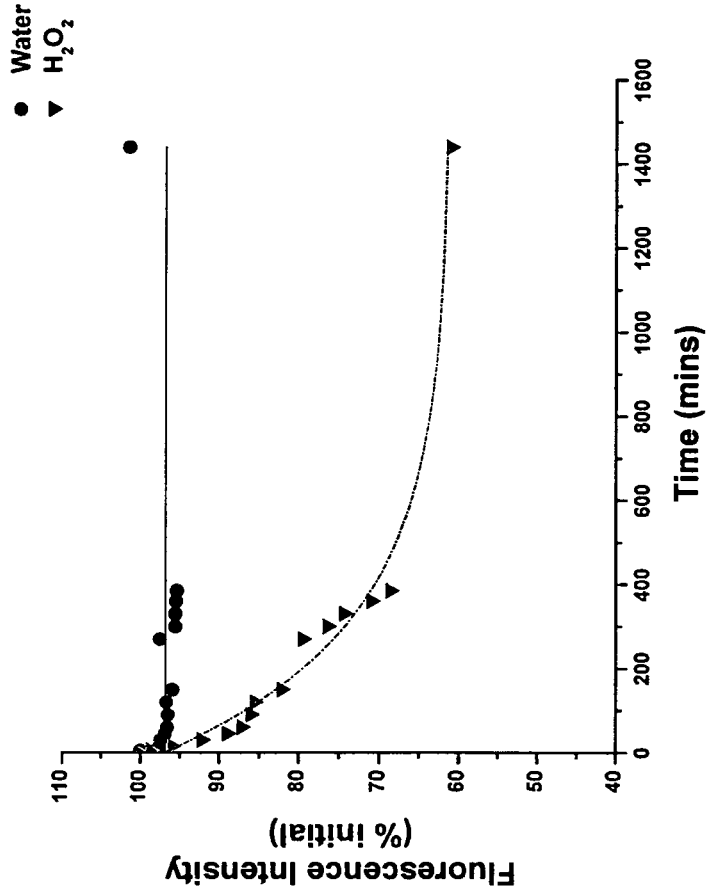
FIG. 3 is a graph of the time-dependent fluorescence of the nanoparticles (HBPE-DiI) in the presence of reactive oxygen species (ROS).

FIG. 3 is a graph of the time-dependent fluorescence of the imaging nanoparticles in the presence of hydrogen peroxide. One hundred percent fluorescence intensity in water decreases to approximately 60% fluorescence intensity in 1400 minutes in the presence of hydrogen peroxide, a generator of reactive oxygen species (ROS). The photostability of the nanoparticles in water (control), is shown by the fluorescence intensity remaining constant. In contrast, in the presence of hydrogen peroxide ($H_2O_2$ 1 □), the fluorescence emission of the HBPE-DiI nanoparticles decreases, due to the presence of ROS generated by $H_2O_2$ decomposition that oxidizes the dye and therefore reduces its fluorescence intensity.

Figure 4:
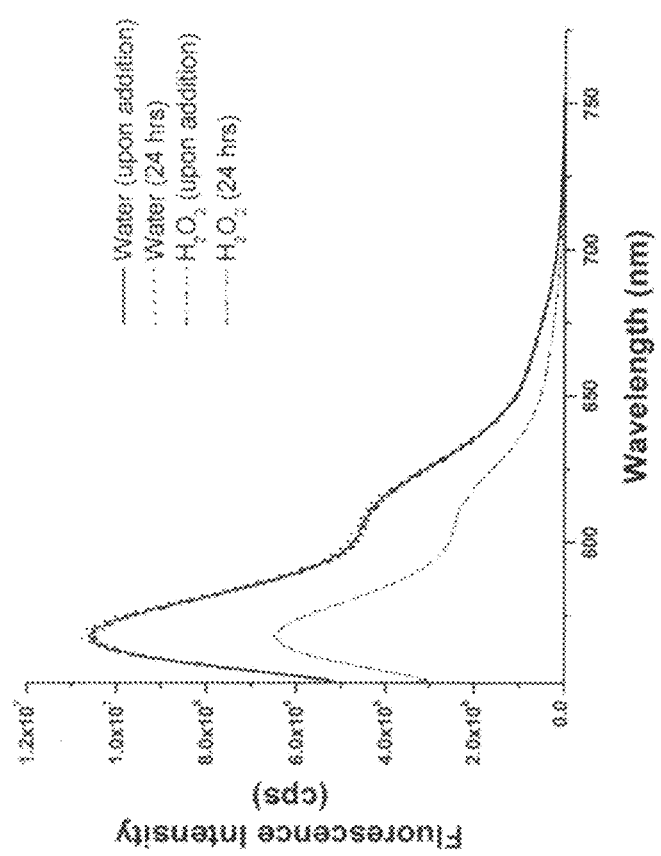
FIG. 4 is a graph showing the decrease in the fluorescence emission of nanoparticles after 24 hours in the presence of hydrogen peroxide ($H_2O_2$).

FIG. 4 graphically depicts the decrease in the fluorescence emission of HBPE-DiI nanoparticles after 24 hours in the presence of hydrogen peroxide. Fluorescence emission spectroscopy indicates the stability of the fluorophore nanoparticle (HBPE-DiI) in water and in the absence of ROS. At approximately 300 nm in wavelength, fluorescent intensity is measured at $1.0 \times 10^7$ cps. The fluorescence emission significantly decreases under elevated ROS concentrations due to decomposition of hydrogen peroxide (1 □) and at approximately 300 nm wavelength fluorescence intensity is $6.0 \times 10^6$ cps.

Figure 5:
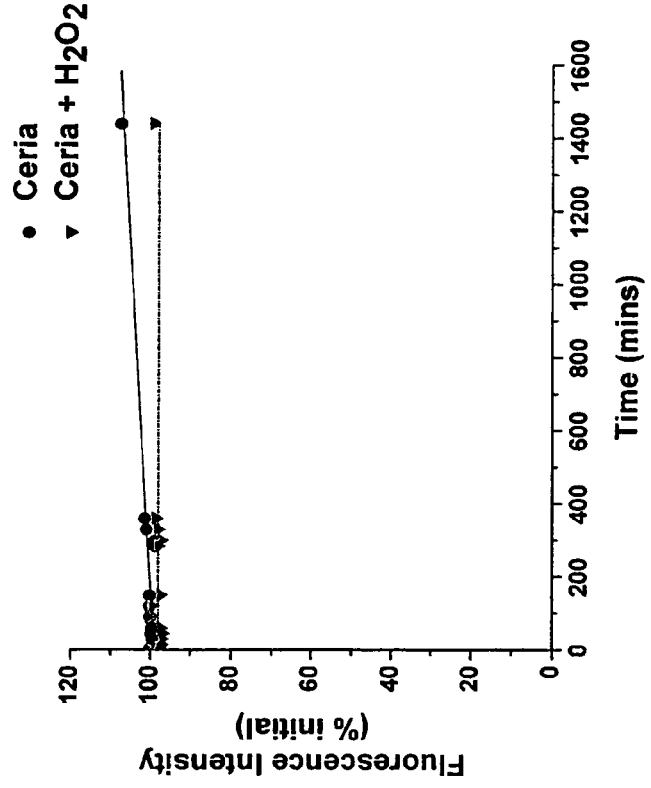
FIG. 5 is a graph of time-dependent nanoparticle fluorescence emission in the presence of nanoceria and ROS in suspension.

FIG. 5 is a graph of the time-dependent HBPE-DiI nanoparticle fluorescence emission in the presence of nanoceria and ROS in suspension. The graph demonstrates that nanoceria facilitates the retention of the device's fluorescence emission (HBPE-DiI) in the presence of hydrogen peroxide (100), because nanoceria is able to scavenge the generated ROS therefore preserving the fluorescence emission of the dye. Over a period of approximately 1400 minutes, fluorescence intensity remains at approximately 95% of the initial fluorescence. Thus, nanoceria protects the fluorophore DiI containing component from ROS.

Figure 6:
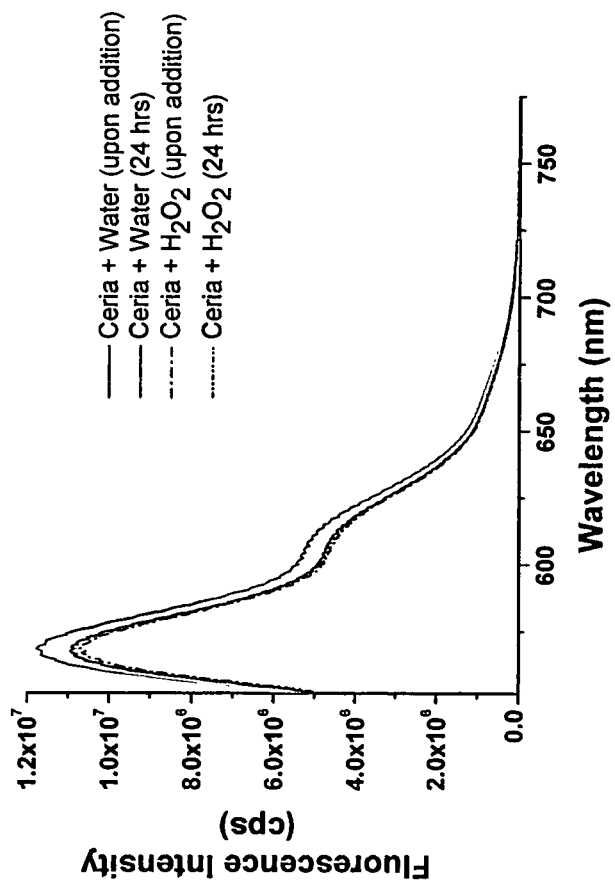
FIG. 6 is a graph of fluorescence intensity of nanoceria particles in water and in $H_2O_2$ showing that nanoceria provides sustained protection from ROS to fluorescent nanoparticles.

FIG. 6 is a graph showing that nanoceria provides sustained protection from ROS to fluorescent nanoparticles. Fluorescence emission spectroscopy supports the hypothesis that the nanoceria component of the device would protect the fluorescence emission of the fluorophore(DiI)-containing component, even in the presence of hydrogen peroxide (1 μM).

Figure 7:
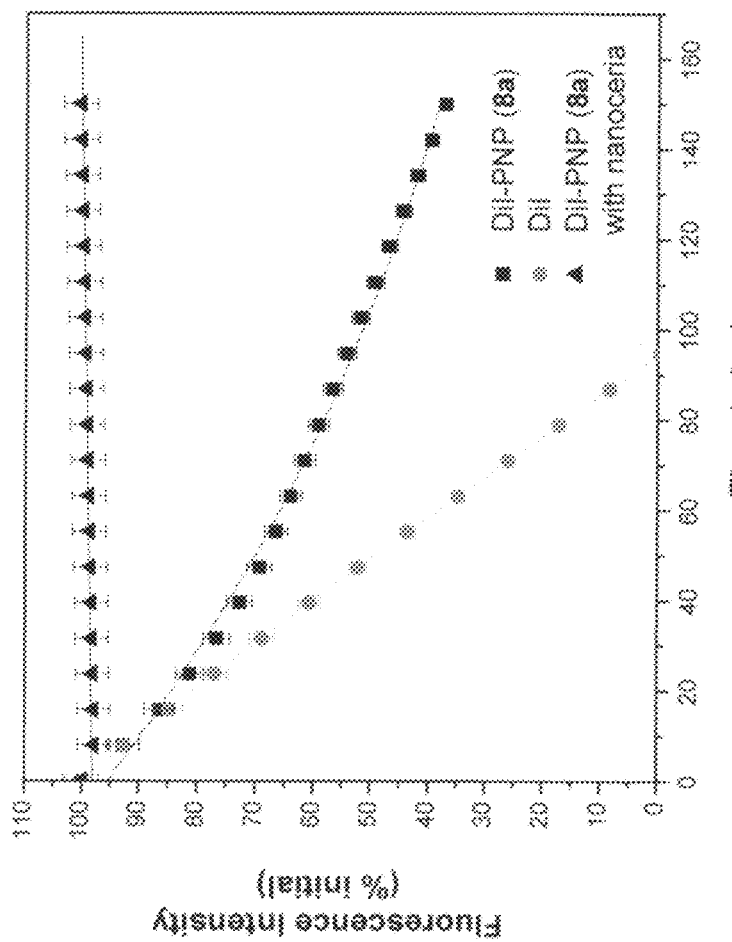
FIG. 7 is a graph of time-dependent retention of the fluorescence emission of fluorescent nanoparticles (HBPE-DiI) by nanoceria after exposure to ultraviolet (UV) radiation.

FIG. 7 is a graph of the time-dependent retention of the fluorescence emission of the HBPE-DiI fluorescent nanoparticle by nanoceria after exposure to UV radiation. In the absence of nanoceria, the non-encapsulated fluorophore (DiI) rapidly loses its fluorescence emission. Encapsulation of the dye (HBPE-DiI) prolongs the fluorescence emission from the fluorophore, but gradually it decreases. Addition of nanoceria to the fluorescent nanoparticles protects fluorescence emission over prolonged exposure to UV radiation. The fluorescence intensity remains at 100% of the initial intensity for over 160 minutes.

Collectively, FIGS. 3-7 demonstrate three important results of testing the two-chamber device in solution. First, in the presence of ROS, fluorescence emission from dyes, such as DiI, rapidly decrease making them suitable probes for ROS monitoring. Second, the addition of nanoceria results in photoprotection of the fluorescence intensity of the dye, protecting the fluorophore from ROS attacks. Third, nanoceria protects the fluorophore from direct damage and ROS generated during UV radiation.

Photographic Evidence of Function of Polyacrylic Acid (PAA) Coated Nanoceria.

The photographs were taken using a small animal imaging station (IVIS, Xenogen). However, these results can be obtained with other optical and fluorescence instrumentation, including other proprietary small animal imaging stations.

Figure 8A:
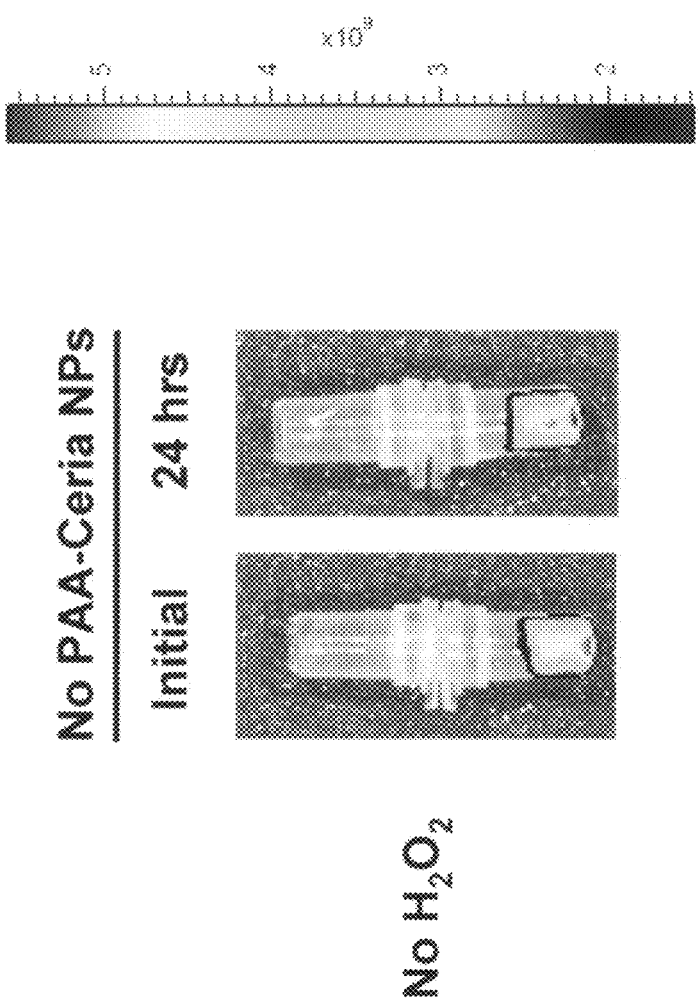
FIG. 8A shows a cerium oxide nanoparticle-based device wherein the fluorescence emission of the DiI-Dex-IO nanoparticles is stable under physiological conditions (no ROS i.e., no $H_2O_2$, pH 7) as determined after 24 hour incubation.

FIG. 8A shows that when there is no coating on nanoceria particles and no $H_2O_2$ is present, the fluorescence emission of the DiI-Dex-IO nanoparticles is constant/unaltered.

Figure 8B:
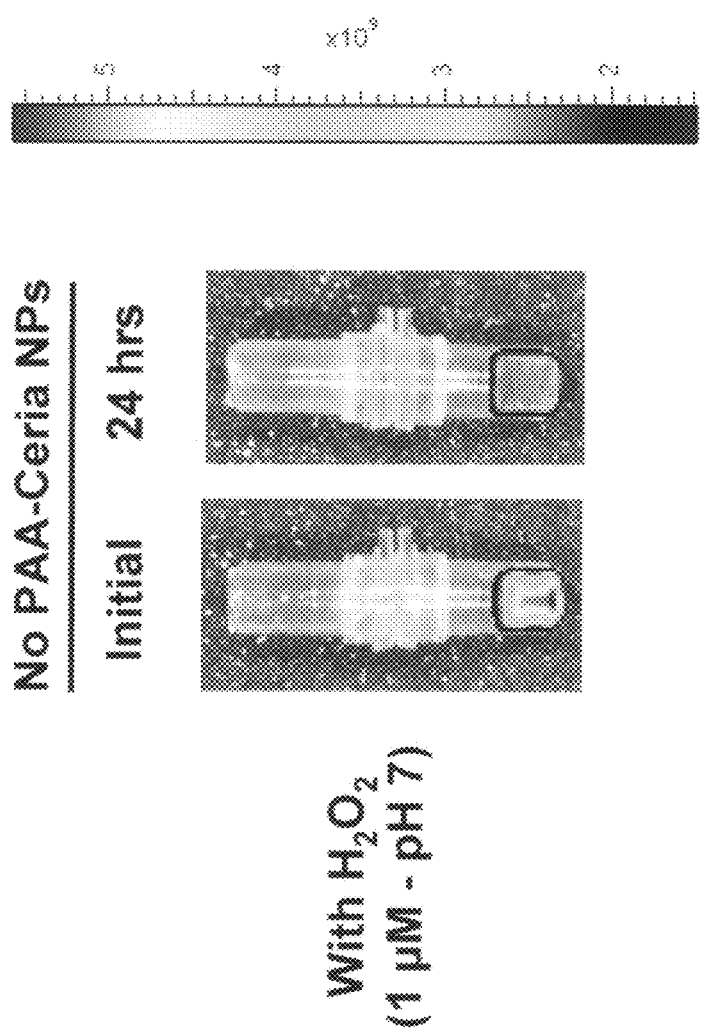
FIG. 8B shows a cerium oxide nanoparticle-based device wherein the fluorescence emission of the DiI-Dex-IO nanoparticles is diminished after 24-hour-long exposure to ROS ($H_2O_2$, pH 7).

In contrast, FIG. 8B shows that a nanoparticle-based device with no coating on nanoceria and with 1 μM $H_2O_2$ present in a solution with a pH value of 7 exhibits change in the fluorescence emission of its DiI-Dex-IO nanoparticles after 24-hour exposure to ROS; there is a significant loss in fluorescence emission from the device.

Figure 8C:
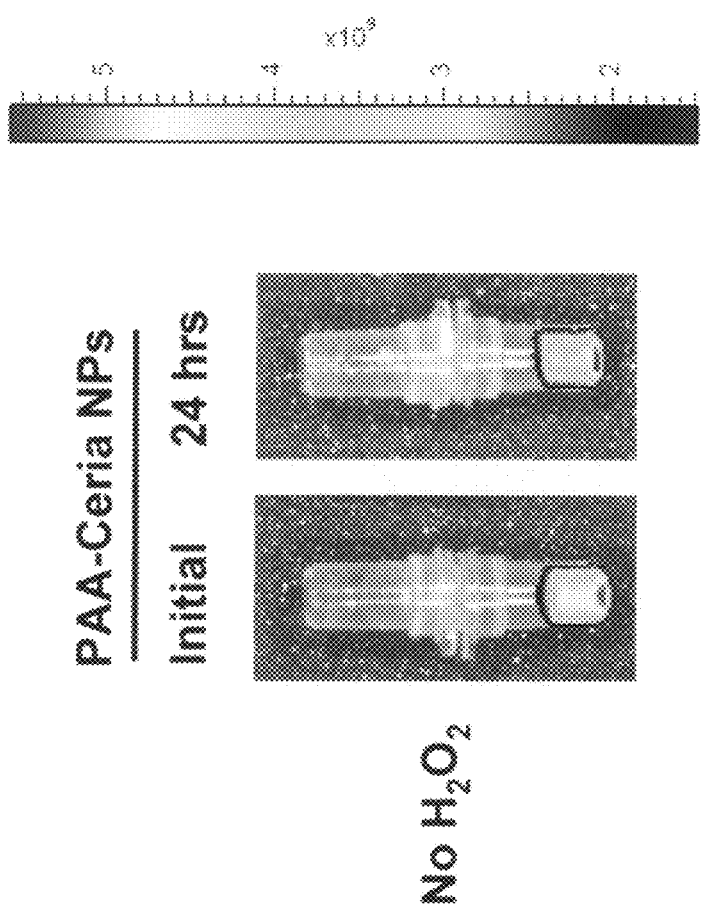
FIG. 8C shows that a cerium oxide nanoparticle-based device with polymer-coated, polyacrylic acid (PAA), nanoceria does not affect the fluorescence emission of the DiI-Dex-IO nanoparticles after 24-hour-long incubation at physiological conditions (no ROS i.e., no $H_2O_2$, pH 7)
Figure 8D:
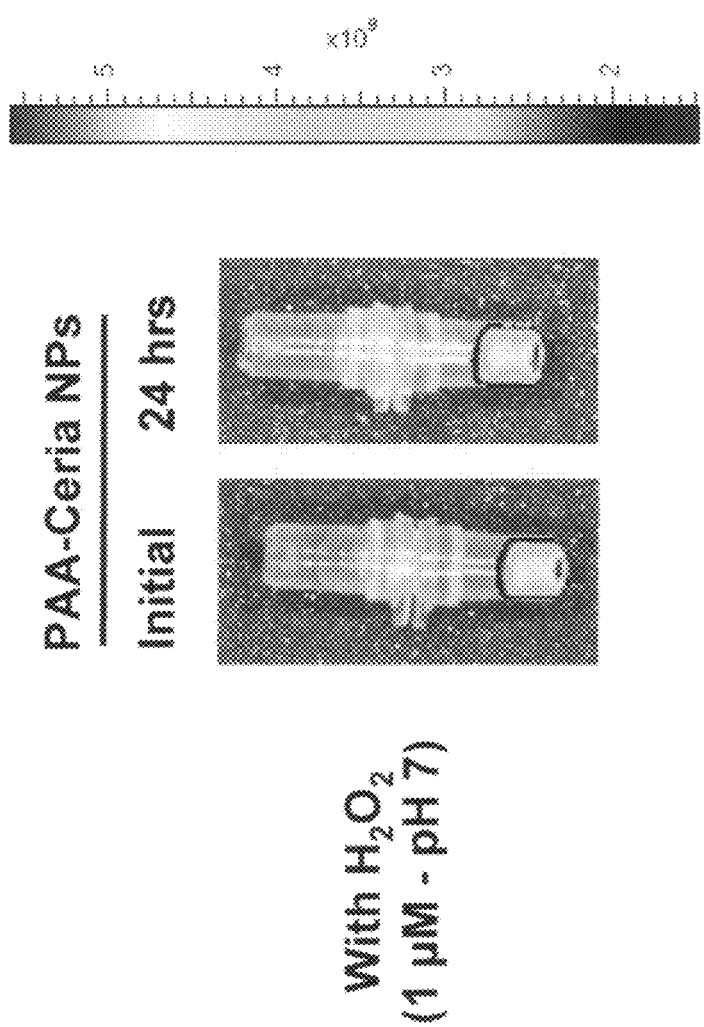
FIG. 8D shows that a cerium oxide nanoparticle-based device with polymer-coated, polyacrylic acid (PAA), nanoceria does not affect the fluorescence emission of the DiI-Dex-IO nanoparticles from ROS after 24-hour exposure to $H_2O_2$ at pH 7.

FIG. 8C shows that polymer-coated nanoceria (e.g., with polyacrylic acid (PAA) coating), does not affect the fluorescence emission of the D11-Dex-IO nanoparticles. Most importantly as shown in FIG. 8D, polymer-coated nanoceria protects the fluorescence emission of the DiI-Dex-IO nanoparticles from ROS after 24-hour exposure to $H_2O_2$ at pH 7; there is no change in fluorescence emission.

Thus, original photographs of the device (FIGS. 8A, 8C and 8D) show that nanoceria does not affect DiR-Dex-IO fluorescence emission under physiological conditions, and the fluorescence of the DiR-Dex-IO is stable over time, either with or without nanoceria. However, ROS due to $H_2O_2$ does cause a decrease in the fluorescence emission of DiR-Dex-IO when nanoceria is not present (FIG. 8B); but in the presence of nanoceria, fluorescence is protected as nanoceria scavenges ROS at pH 7; the photobleaching effect of hydrogen peroxide is abrogated and fluorescence emission is retained (FIG. 8D). Incubations for 24 hours were performed to check stability and long-term exposure to ROS.

Figure 9A:
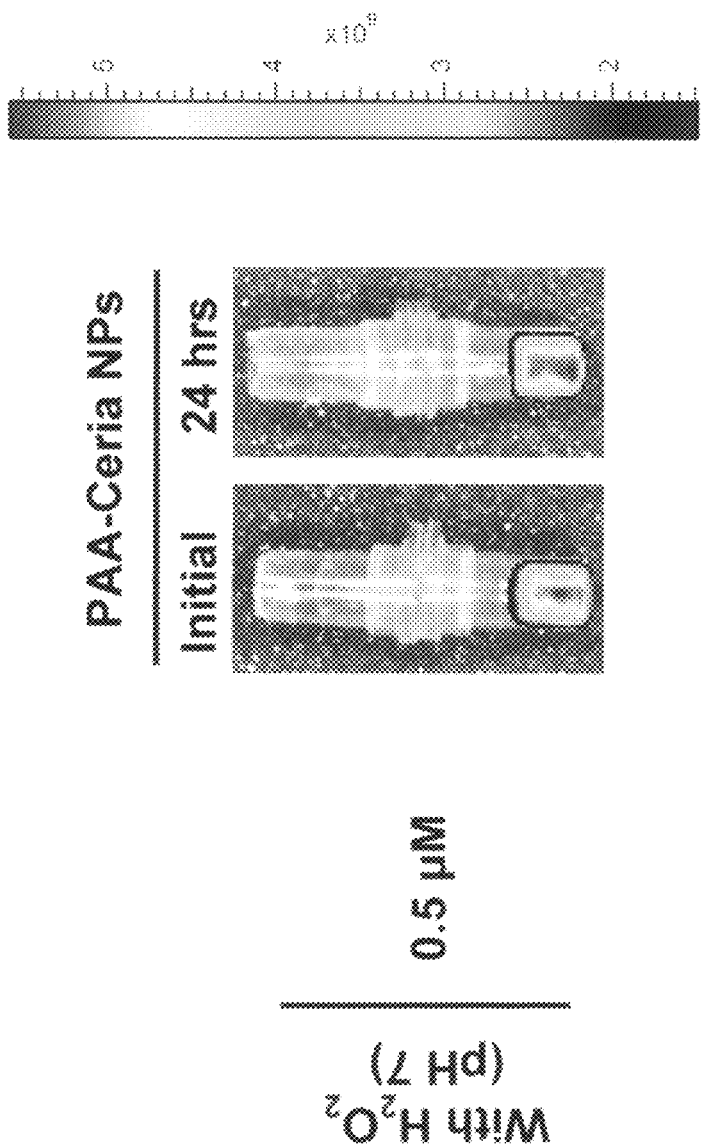
FIGS. 9A, 9B, 9C shows that a cerium oxide nanoparticle-based device with polymer-coated, polyacrylic acid (PAA), nanoceria protects the fluorescence emission of the DiI-Dex-IO nanoparticles from ROS for a period of 24 hours at physiological $H_2O_2$ concentrations of 0.5 µM, 1.5 µM and 3.0 µM in solutions with a pH value of 7.
Figure 9B:
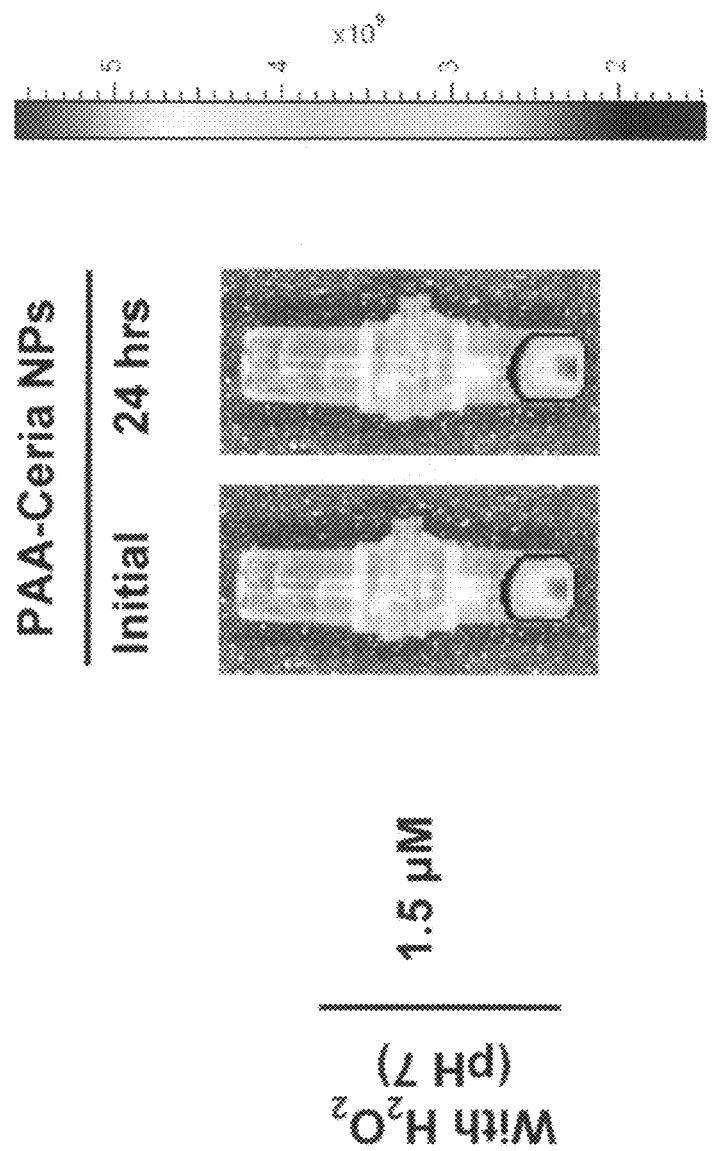
Figure 9C:
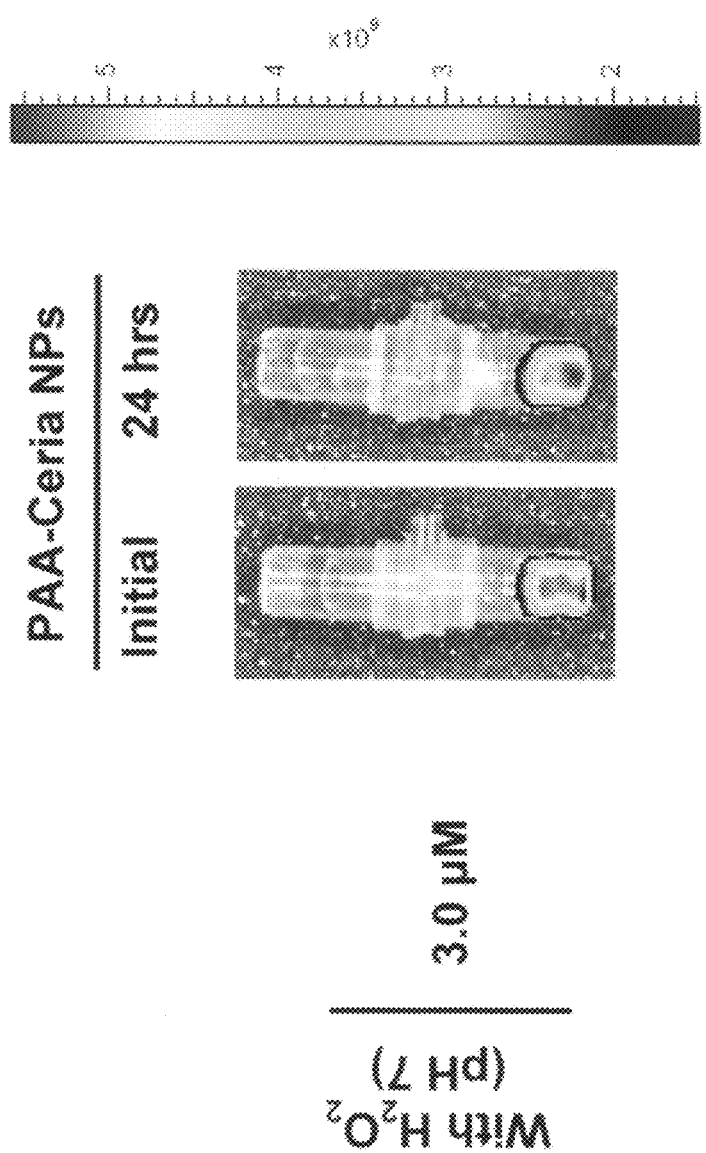

FIGS. 9A-9C show that a cerium oxide nanoparticle-based device with polymer coated, polyacrylic acid (PAA), nanoceria protects the fluorescence emission of the DiI-Dex-IO nanoparticles from ROS after 24-hour exposure at physiological $H_2O_2$ concentrations of 0.5 μM (FIG. 9A), 1.5 μM (FIG. 9B) and 3.0 μM (FIG. 9C) in solutions with a pH value of 7. Stated in another way, under physiological ROS levels ($[H_2O_2]$=0-3 μM), nanoceria protects the fluorescence emission of the DiI-Dex-IO nanoparticles of an implantable therapeutic device.

Figure 10A:
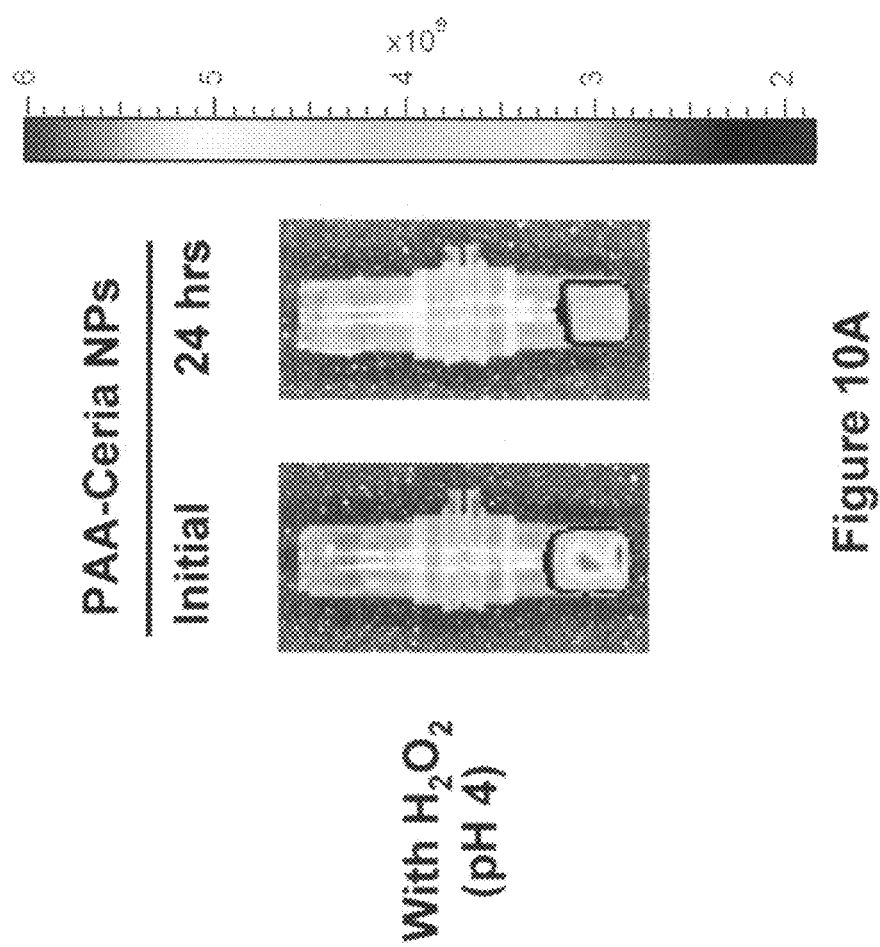
FIG. 10A shows that a cerium oxide nanoparticle-based device with polymer-coated, polyacrylic acid (PAA), nanoceria does not protect the fluorescence emission of the DiI-Dex-IO nanoparticles from ROS for a period of 24 hours at a non-physiological pH value of 4 in the presence of $H_2O_2$, allowing imaging of ROS generation.

FIG. 10A shows that a cerium oxide nanoparticle-based device with polymer coated, polyacrylic acid (PAA), nanoceria does not protect the fluorescence emission of the DiI-Dex-IO nanoparticles from ROS after 24-hour exposure to $H_2O_2$ at a non-physiological pH value of 4, allowing imaging of ROS generation.

FIG. 10B shows that a cerium oxide nanoparticle-based device with polymer coated, polyacrylic acid (PAA), nanoceria does not protect the fluorescence emission of the DiI-Dex-IO nanoparticles from ROS after 24-hour exposure under inflammatory conditions simulated by high levels of ROS, generated by $H_2O_2$.

Thus, FIGS. 10A and 10B show that under conditions of elevated inflammation ($[H_2O_2] \geq 6$ μM) or nanoceria's pH-dependent catalytic inactivation (acidic pH, i.e., 4.0), the device's fluorescence emission from DiI-Dex-IO nanoparticles decreases. It is worth mentioning that in vivo chronic inflammation is often associated with a decrease in the pH, thus it can contribute to decreased fluorescence emission. Hence, these data demonstrate that the device's "switch off" occurs specifically under non-physiological conditions, such as, high ROS and/or low pH, making the device suitable for in vivo imaging of inflammation.

In other words, during normal levels of inflammation the device will be responsive and nanoceria in the ROS-scavenging chamber will be able to scavenge ROS, preserving the monitoring chamber's fluorescence emission herein designated as the ON state. However, during chronic inflammation nanoceria will not be able to scavenge ROS and the device's performance will be affected, leading to decrease in fluorescence emission herein designated as the OFF state. Therefore, the decrease in fluorescence emission will be an indicator for the physician to take further action, minimizing inflammation and preventing systemic tissue damage.

Figure 11:
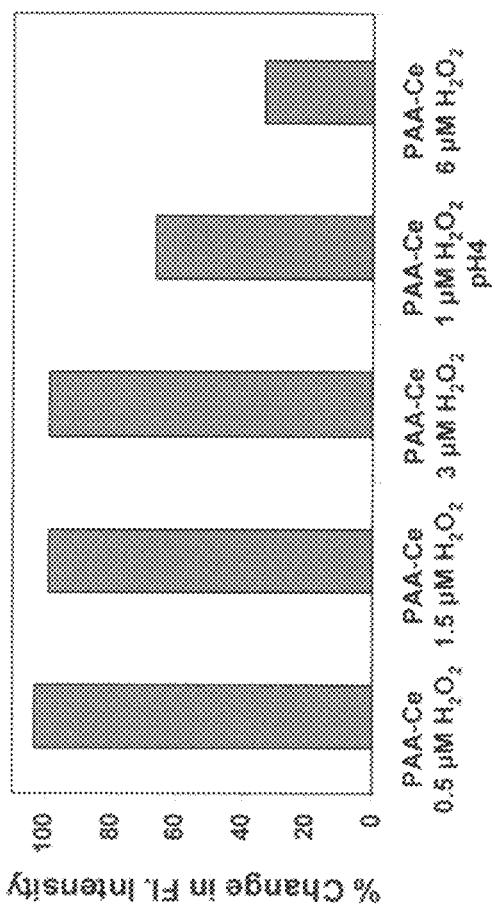
FIG. 11 is a graph showing the percent change in fluorescent intensity of a cerium oxide nanoparticle-based device with polymer-coated, polyacrylic acid (PAA), nanoceria wherein the fluorescence emission of the DiI-Dex-IO nanoparticles changes with $H_2O_2$ concentrations of 0.5 µM, 1.5 µM, 3.0 µM, 1.0 µM at pH value 4 and 6.0 µM.

FIG. 11 is a graph of the change in fluorescence intensity under physiological and non-physiological conditions. The percentage decrease in the device's fluorescence emission (DiI-Dex-IO) upon polymer-coated nanoceria's ROS-scavenging inactivation was from approximately 100% intensity when $H_2O_2$ concentrations were 0.5 μM, 1.5 μM and 3.0 μM. The fluorescence emission intensity decreased to approximately 60% intensity when $H_2O_2$ concentrations were 1.0 μM at pH value 4. Fluoresence emission intensity decreased to approximately 30% when $H_2O_2$ concentrations were 6.0 μM, at conditions of elevated ROS levels.

FIG. 11 shows that in the presence of nanoceria, physiological ROS levels do not affect the device's fluorescence. This indicates the specificity and sensitivity of the device. However, in the presence of nanoceria, elevated ROS levels associated with aberrant inflammation cause decrease in fluorescence emission (FIG. 11). Thus, the device can be used for the monitoring of the inflammatory response.

Also, in the presence of nanoceria and low pH, fluorescence emission decreases in the presence of ROS (FIG. 11). Hence, the device can be used for the monitoring of ROS generation during chemotherapy or gastrointestinal inflammation, such as ulcerative colitis, inflammatory bowel disease, and Crohn's disease.

Study of Factors that Reduce Fluoresence Emission of Fluorophores

To corroborate that the reduction in the fluorophore emission is due to ROS-induced damage and not due to the acidic pH, we performed the following experiments with the fluorophore being in physiological (pH 7.5) and acidic (pH 4) levels. No nanoceria was used in these studies in order to ascribe the role of pH on fluorophore stability.

Figure 12:
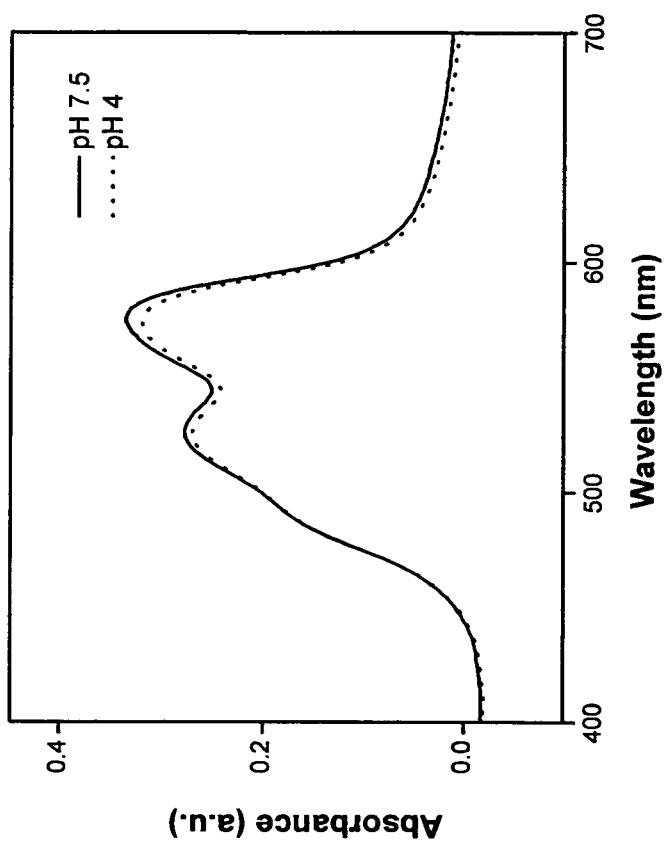
FIG. 12 is a graph of the stability of the non-encapsulated fluorophore (DiI) at physiological and acidic pH values, pH 7.5 and pH 4, respectively.

FIG. 12 shows that the non-encapsulated fluorophore (Dip has an almost identical absorbance curve at physiological (pH 7.5) and acidic (pH 4) pH, indicating stability of the fluorophore under both pH values. Ultraviolet (UV)-vis spectroscopy reveals the fluorophore's (DiI) stability at physiological and acidic pH solutions, in the absence of hydrogen peroxide. Therefore, changes in fluorescence emission are due to exposure to ROS and not due to the low pH per se.

Figure 13:
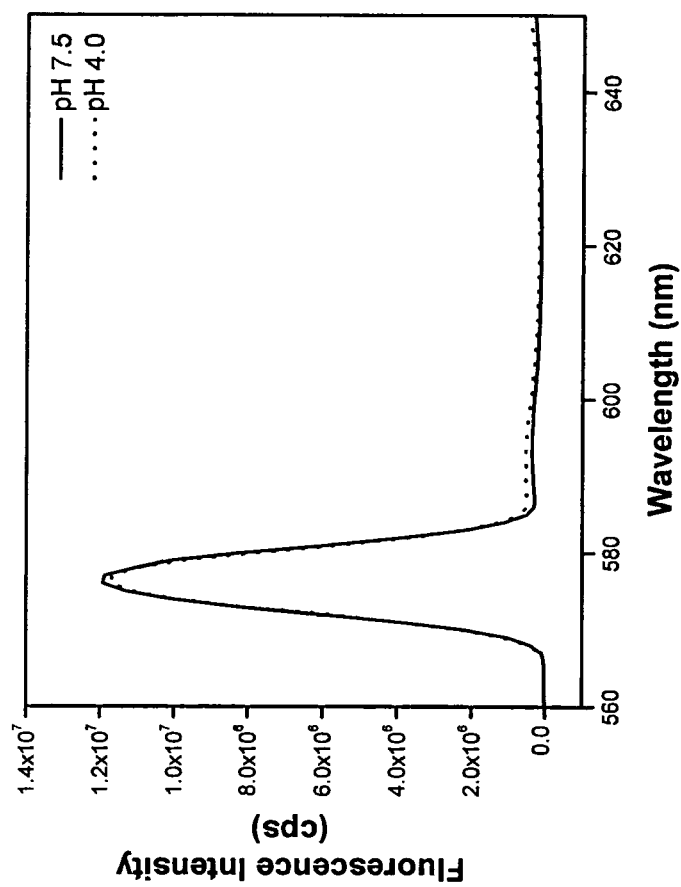
FIG. 13 is a graph of the fluorescence emission stability of the non-encapsulated fluorophore (DiI) at physiological and acidic pH values, pH 7.5 and pH 4, respectively

FIG. 13 is a graph of fluorescence intensity and shows fluorescence emission stability of the non-encapsulated fluorophore (DiI) at physiological (pH 7.5) and acidic (pH 4) values. Fluorescence emission spectroscopy indicates that the device's fluorophore emission (DiI) is pH-independent. No changes are observed in the emission profile between physiological and acidic pH.

Thus, the fluorophore's structural integrity is not affected by the pH, as indicated by the similar UV-vis spectra obtained at different pH levels. Also, the fluorescence emission profile of the fluorophore is not affected by pH levels, corroborating that the changes are caused after exposure to ROS.

Factors that Affect Regeneration of Nanoceria Component.

Next, it was determined if nanoceria in the ROS-scavenging chamber of the device has the ability to regenerate after exposure to ROS. Utilizing X-ray photoelectron spectroscopy (XPS), we deduced the valence state of the nanoceria's cerium ($Ce^{+3}/Ce^{+4}$) is measured at different pH levels and ROS levels. Proof of regeneration is shown when $Ce^{+3}$ ions are present at a concentration level above approximately 55% and $Ce^{+4}$ ions are present in a concentration level greater than approximately 40% of the total cerium ions.

FIG. 14 is a chart showing the percentage of each valence state of the cerium element in the polymer-coated nanoceria component at pH 7; pH 7 and 1.0 μM $H_2O_2$; pH 4 and 1.0 μM $H_2O_2$; pH 7 and 6.0 μM $H_2O_2$.

XPS analysis indicates that at low ROS concentrations, such as 1 μM $H_2O_2$, the device's nanoceria has the ability to regenerate. At acidic Ph, such as pH 4, or high inflammatory conditions (high ROS), such as 6 μM $H_2O_2$, nanoceria loses its autoregenerative property, leading to a decrease in the device's fluorescence emission, as the DiI-Dex-IO fluorophore is susceptible to ROS attacks.

Multi-Modal DiR-Dex-IO Nanoparticle for a NIR-Fluorescent/MRI Monitoring Chamber.

Figure 15:
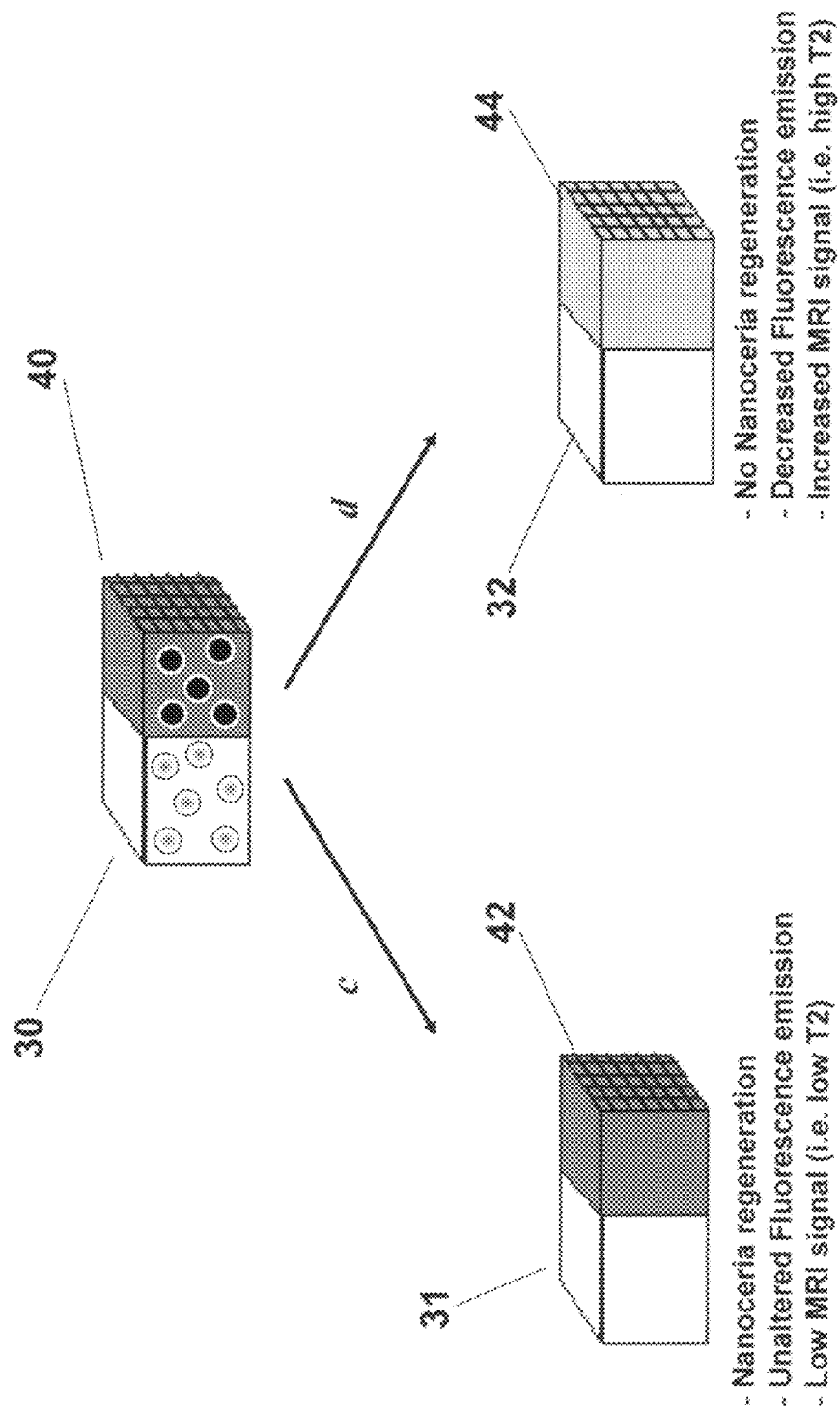
FIG. 15 is a schematic depiction of the detection of ROS with a device consisting of a nanoceria ROS-scavenging chamber and a multimodal DiR-Dex-IO nanoparticle (NIR-fluorescent/MRI) monitoring chamber.

Multimodal monitoring of inflammation through a device, consisting of a ROS-scavenging chamber 30 with nanoceria and a multimodal monitoring chamber 40 with DiR-doped dextran-coated iron oxide nanoparticles is shown in FIG. 15. The use of a multimodal DiR-Dex-IO nanoparticle allows magnetic resonance imaging (MRI), by the monitoring chamber and represents a second embodiment of the present invention.

Multimodal monitoring of inflammation is useful when under elevated reactive oxygen species (ROS) levels or loss of nanoceria regeneration; the fluorescence emission and the magnetic resonance imaging of the nanocomposite changes and the ROS beacons facilitate tracking with the use of chemiluminescence, magnetic relaxation or X-ray contrast agents.

In FIG. 15, the ROS scavenging chamber 30 is positioned adjacent to multimodal monitoring chamber 40 and held in position by an adhesive or glue. In the two chamber device, there is no exchange of particles between the two chambers. Under conditions of no or mild inflammation c, the device's cerium oxide nanoparticle component (nanoceria) in chamber 31 scavenges the generated ROS, as ROS production is either nominal or transient, leading to preservation of the device's fluorescence emission in chamber 42. However, under conditions of chronic persistent inflammation d, nanoceria in chamber 32 does not have the ability to regenerate quickly enough, thus the excess ROS dim or switch off the device's fluorescence emission in chamber 44, due to the fluorophore's sensitivity to ROS. However, due to the use of iron oxide nanoparticles in the monitoring chamber 40 and the benefits of magnetic resonance imaging (MRI), there is an increased MRI signal from the monitoring chamber 44.

Iron oxide nanoparticles are selected because of the wide clinical use in tomographic image acquisitions, and excellent deep tissue resolution and penetration. DiR is used, which is a near-infrared fluorophore tht can be used for optical imaging avoiding tissue autofluorescence. The iron oxide particles were also dextran coated (Dex-IO), as they are widely used in the clinic as MRI contrast agents. Hence, encapsulated DiR in Dex-IO nanoparticles (DiR-Dex-IO) are proven to have a dual probe for potentially clinical in vivo inflammation monitoring.

Figure 16A:
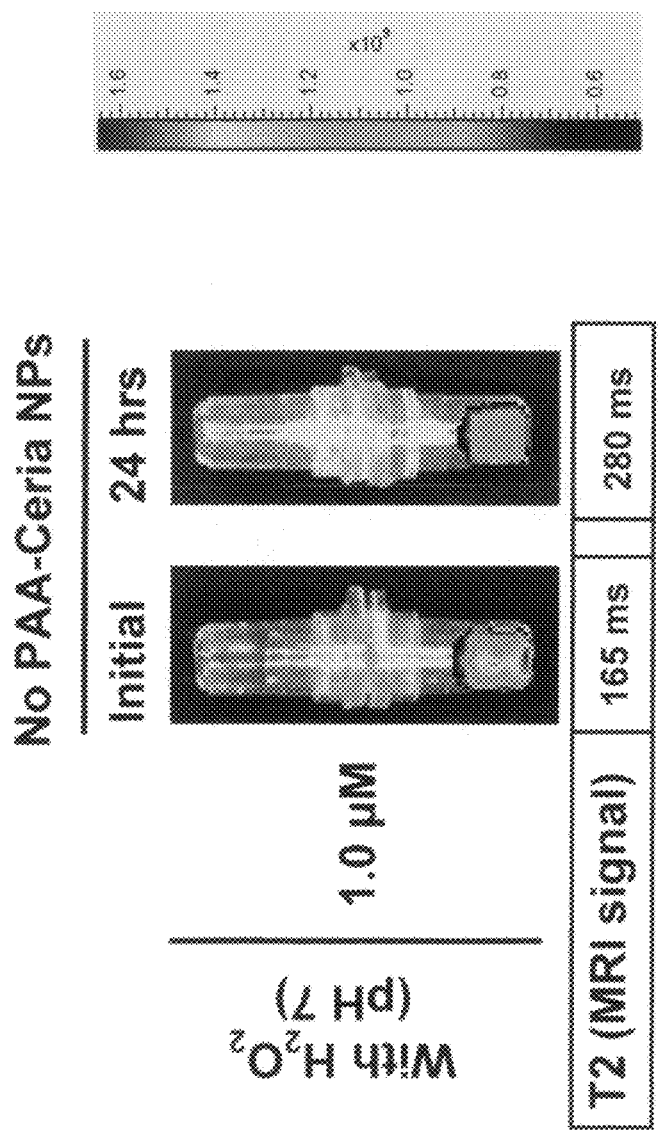
FIG. 16A shows that a cerium oxide nanoparticle-based device with no polyacrylic acid (PAA) coated nanoceria and with multimodal DiR-Dex-IO nanoparticles is sensitive towards ROS generated by H$_2$O$_2$ (1.0 µM), after 24-hour exposure to H$_2$O$_2$ in pH 7 (physiological pH). The ROS beacons are multimodal and can sense ROS via changes in fluorescence and T2 relaxation times (T2$_{in}$=165 ms, T2$_{fin}$=280 ms).
Figure 16B:
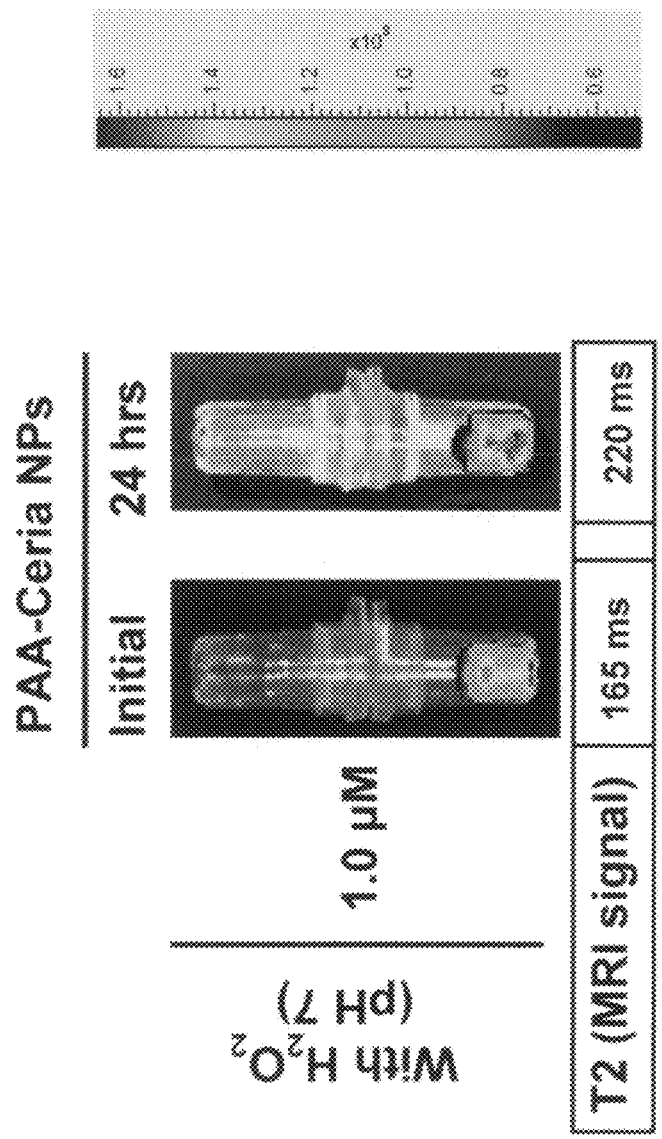
FIG. 16B shows that a cerium oxide nanoparticle-based device with both polymer-coated, polyacrylic acid (PAA) nanoceria and multimodal DiR-Dex-IO nanoparticles can differentiate physiological ROS levels generated by H$_2$O$_2$ (1 µM), after 24-hour exposure to H$_2$O$_2$ in pH 7 (physiological pH). At physiological pH and ROS levels, the ROS beacons retain their fluorescence emission intensity and a small change in the T2 relaxation times are observed (T2$_{in}$=165 ms, T2$_{fin}$=220 ms).

FIG. 16A shows that in the absence of nanoceria, the multimodal DiR-Dex-IO nanoparticles can sense ROS generated by $H_2O_2$ (1.0 μM), after 24-hour exposure to $H_2O_2$ in pH 7 (physiological pH) via changes in fluorescence and T2 relaxation times ($T2_{in}$=165 ms, $T2_{fin}$=280 ms). FIG. 16B shows that in the presence of nanoceria, the multimodal DiR-Dex-IO nanoparticles can differentiate physiological ROS levels generated by $H_2O_2$ and the ROS beacons retain their fluorescence emission intensity with a small change in the T2 relaxation times ($T2_{in}$=165 ms, $T2_{fin}$=220 ms). Thus, it was determined that a physician using the nanocomposite device will not receive a false positive signal when ROS levels and pH are physiological.

In the presence of nanoceria, DiR-Dex-IO nanoparticles retain near-infrared fluorescence and T2 relaxation does not change significantly, under exposure to ROS.

In the absence of nanoceria, exposure to ROS leads to a decrease in the DiR-Dex-IO nanoparticle fluorescence where the T2 relaxation increases. This indicates that the device can be used in the clinic for inflammation monitoring with MRI and optical imaging methods. The changes in the T2 relaxation times upon exposure to ROS are attributed to nanoparticle clustering.

Figure 18:
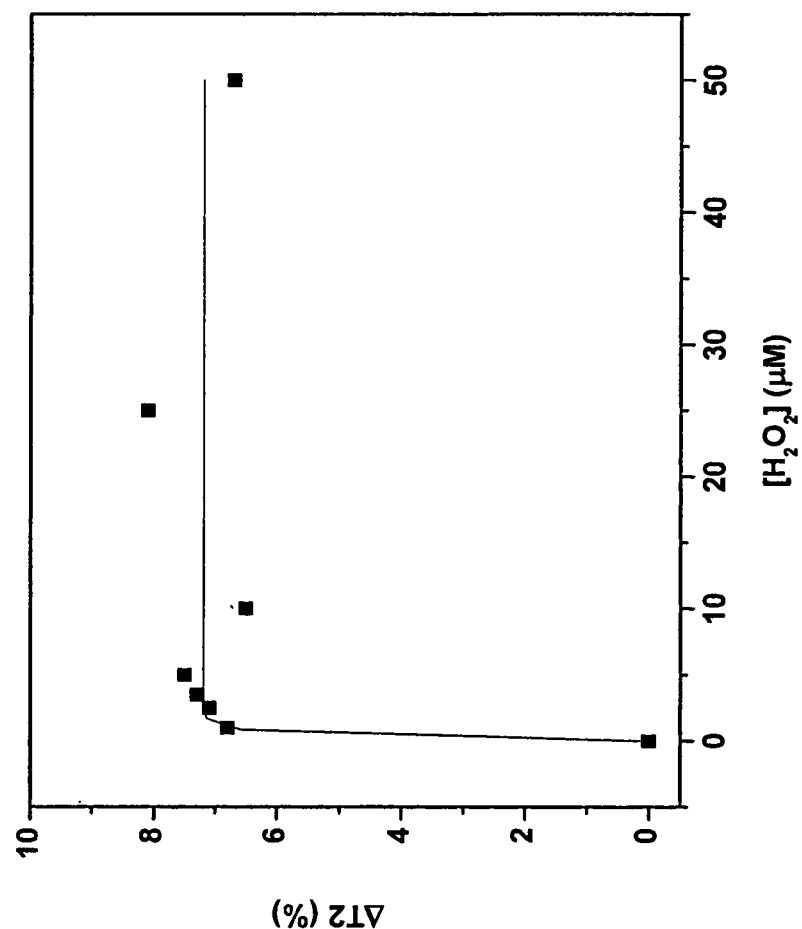
FIG. 18 shows the corresponding change in T2 relaxation signal (MRI signal) upon addition of H$_2$O$_2$.

To elucidate the changes in the T2 relaxation times, Dynamic Light Scattering (DLS) was employed. Results indicate that in the absence of hydrogen peroxide the nanoparticles' average diameter size was 135 nm (FIG. 17A). However, under elevated ROS levels generated by $H_2O_2$ and without nanoceria in the solution to scavenge them, the nanoparticles' average size significantly increased, demonstrating micron-size cluster aggregation with an average particle size of 2860 nm in diameter. (FIG. 17B). Hence, this phenomenon justifies the prominent changes in the relaxation times under inflammatory conditions with elevated ROS and no nanoceria. Finally, we assessed the multimodal DiR-Dex-IO nanoparticles' sensitivity towards ROS, observing that even at low concentrations of $H_2O_2$ the nanoparticles could induce prominent shifts in the T2 relaxation times (FIG. 18) which can be detected by MRI. This indicates that these nanoparticles are sensitive ROS imaging probes, thus even slightly aberrant concentrations of ROS could "turn" the nanoparticles' imaging switch and change the T2 relaxation time.

Figure 19:
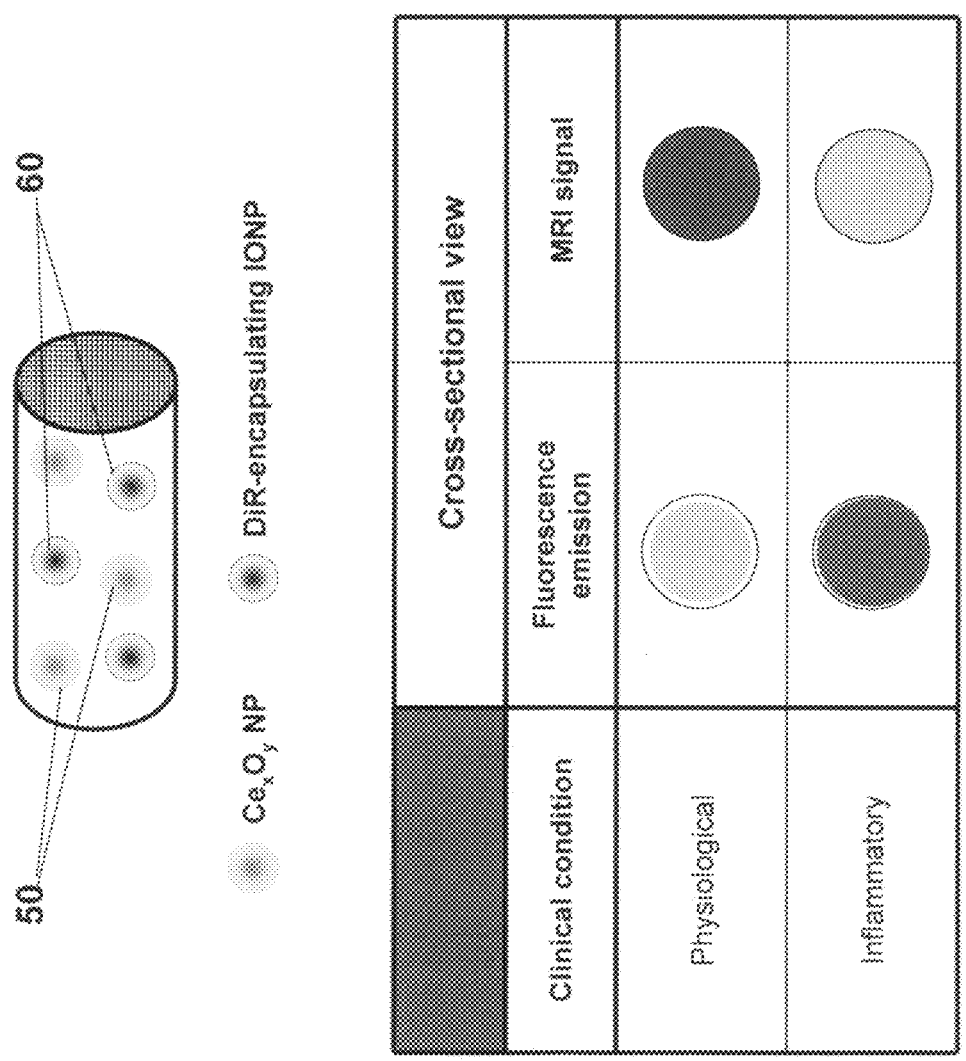
FIG. 19 is a conceptual diagram of the in vivo inflammation monitoring device of the present invention having a single chamber, which also shows the cross-sectional view of the device's fluorescence and MRI response to physiological and non-physiological conditions.

FIG. 19 is a conceptual diagram of the in vivo inflammation monitoring device of the present invention having a single chamber which is a second embodiment of the device of the present invention. The first embodiment has two chambers that are not communicating; a first chamber for the ROS scavenger and a second chamber for monitoring clinical conditions. The design of the first embodiment is to minimize potential fluorophore quenching by nanoceria. However, preliminary results with a nanocomposite consisting of nanoceria and fluorophore-containing nanoparticles indicated no quenching or photostability issues. Therefore the second embodiment is a single chamber device containing the reagents, such as nanoceria and DiR-IO-Dex or a nanocomposite.

The reactive oxygen species (ROS) scavenger particles 50 and the imaging agent particles 60 can be interspersed in one chamber. If there are no inflammatory conditions, the nanoceria particles regenerate and fluorescence emission of the imaging agent occurs.

In the presence of persistent inflammatory conditions, the nanoceria particles do not regenerate and the fluorescence emission of the imaging agent is extinguished.

Dimensions of the device provided by the present invention are given only as an illustration, not as a limitation. A macroscale device is approximately 2 centimeters (cm) in length and approximately 0.4 cm in diameter. A miniature device is approximately 2-4 millimeters (mm) in length and approximately 1 mm in diameter.

Figure 20:
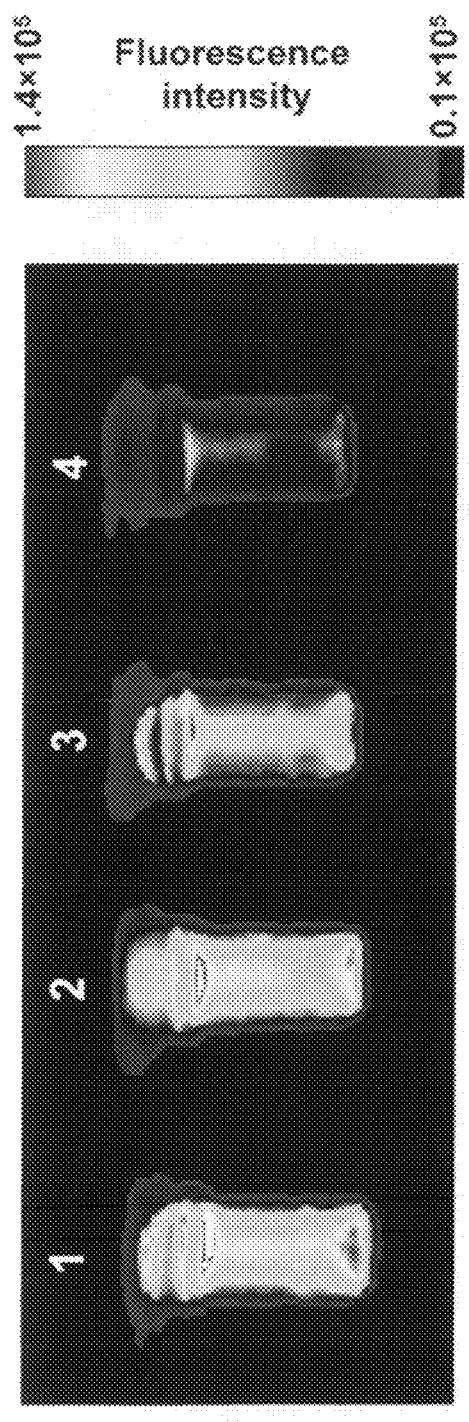
FIG. 20 is a side-view of the fluorescence image of the single-chamber device consisting of polymer-coated, polyacrylic acid (PAA) nanoceria and DiR-Dex-IO nanoparticles after 24-hour-long incubation at physiological conditions (1: no ROS i.e. no H$_2$O$_2$, pH 7), at a physiological H$_2$O$_2$ concentration (2: 1 µM H$_2$O$_2$, pH 7), at a non-physiological inflammatory H$_2$O$_2$ concentration (3: 6 µM H$_2$O$_2$, pH 7), and at a non-physiological chronic inflammatory H$_2$O$_2$ concentration and non-physiological pH (4: 6 µM H$_2$O$_2$, pH 4).

FIG. 20 is a side-view of the fluorescence image of the single-chamber device consisting of polymer-coated, polyacrylic acid (PAA) nanoceria and DiR-Dex-IO nanoparticles after 24-hour-long incubation at physiological conditions. In FIG. 20, image 1 is the control that shows bright fluorescence intensity with no ROS present, i.e. no $H_2O_2$ at pH 7. At a physiological $H_2O_2$ concentration, image 2 also shows bright fluorescence intensity when the device is used in an environment with 1 µM $H_2O_2$ at pH 7. At a non-physiological inflammatory $H_2O_2$ concentration, image 3 shows a diminished fluorescence intensity in a range of approximate $0.9-1.0\times10^5$ in an environment with 6 µM $H_2O_2$ at pH 7, and at a non-physiological chronic inflammatory level $H_2O_2$ concentration and non-physiological pH (6 µM $H_2O_2$, pH 4), image 4 shows a greatly decreased fluorescence intensity in the range of approximately $0.1-0.3\times10^5$.

Figure 21:
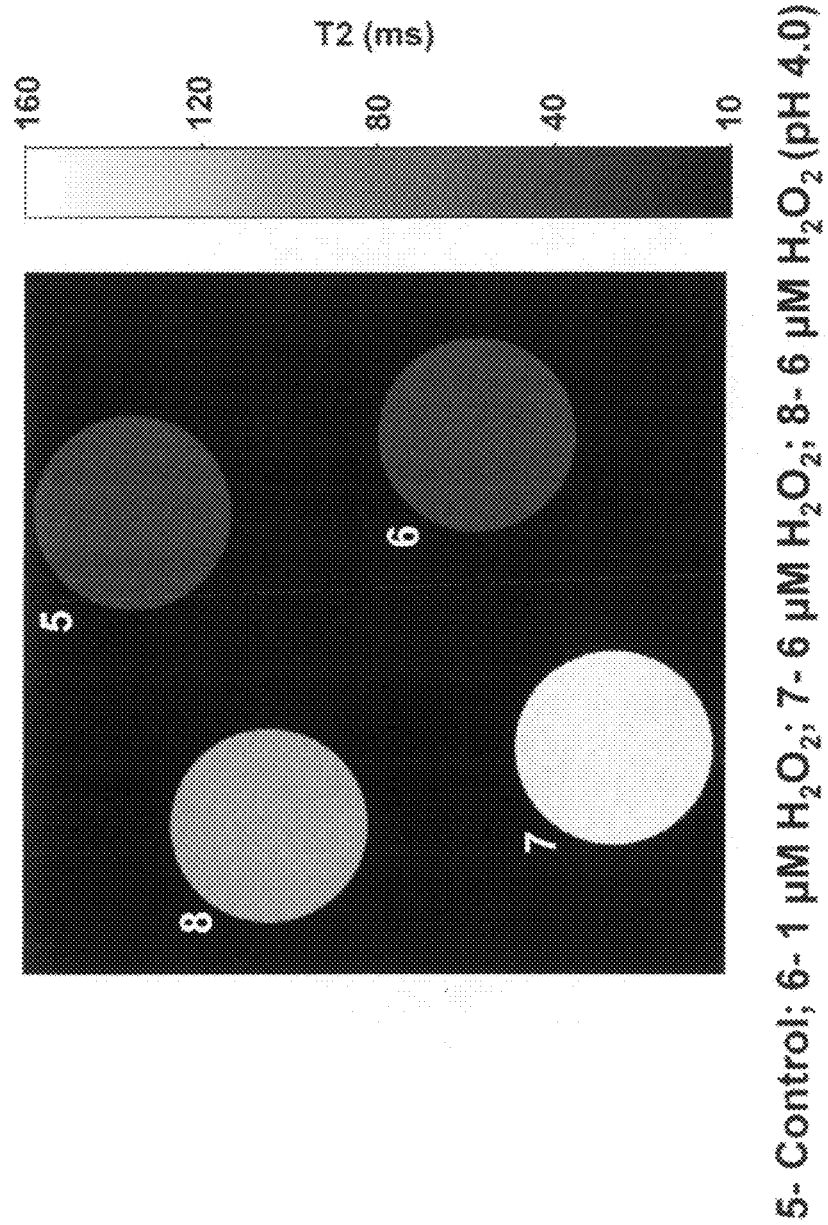
FIG. 21 is a top-view of an MRI image of the single-chamber consisting of polymer-coated, polyacrylic acid (PAA) nanoceria and DiR-Dex-IO nanoparticles after 24-hour-long incubation at physiological (1: no ROS i.e. no H$_2$O$_2$, pH 7; 2: 1 µM H$_2$O$_2$, pH 7) or non-physiological conditions (3: 6 µM H$_2$O$_2$, pH 7; 4: 6 µM H$_2$O$_2$, pH 4).

FIG. 21 is a top-view of an MRI image of the single-chamber consisting of polymer-coated, polyacrylic acid (PAA) nanoceria and DiR-Dex-IO nanoparticles after 24-hour-long incubation at physiological conditions. In FIG. 21, Image 5 is of a T2 relaxation time when there are no ROS i.e. no $H_2O_2$ at pH 7. Image 6 shows T2 relaxation time in the presence of 1 µM $H_2O_2$, at pH 7. T2 relaxation times are shown in non-physiological conditions in Image 7 with 6 µM $H_2O_2$ at pH 7 and in Image 8 with 6 µM $H_2O_2$ at pH 4 which represents the most severe condition with high ROS and low pH. The T2 relaxation times increase as the physiological conditions deviate from normal conditions.

In FIGS. 20 and 21, it is demonstrated that a single chamber device of the present invention distinguishes between physiological and inflammatory conditions. Overall, in the absence of ROS or at moderate ROS levels associated with transient and mild inflammation, the nanoceria in the device is able to scavenge ROS. As a result, fluorescence emission is retained and the T2 relaxation times are comparable to those observed under normal physiological conditions.

However, at high levels of ROS associated with chronic and acute inflammation or under non-physiological conditions manifested with decreases in the pH levels, the fluorescence emission of the device significantly lowers and the T2 relaxation times drastically increase. Thus, under acute conditions, nanoceria cannot scavenge ROS, changing the device's fluorescence and MRI signatures and signaling therapeutic intervention.

In summary, the present invention provides a therapeutic device which is designed to have applications in a broad range of ailments with a pro-inflammatory component, such as Crohn's disease, inflammatory bowel disease, ulcerative colitis, cystic fibrosis, sepsis, cardiovascular disease, arthritis, multiple sclerosis, and Alzheimer's. Furthermore, the use of ROS agents in cancer chemotherapy is reported in several representative publications, such as, Chung, H. Y., et al., "Molecular inflammation: underpinnings of aging and age-related diseases." Ageing Res Rev, 2009. 8(1): 18-30 and Shacter, E., et al., in "Oxidative stress interferes with cancer chemotherapy: inhibition of lymphoma cell apoptosis and phagocytosis" *Blood,* 2000. 96(1): p. 307-13.

Thus, the two-chamber or single chamber device of the present invention can be utilized as an implant in cancer therapeutic regimes. Also, patients with transplants or prosthetic devices may utilize the cerium-oxide-nanoparticle-based device for the in vivo monitoring of the post-operative inflammatory response.

The device of the present invention can be miniaturized and integrated in a prosthetic organ. Moreover, as the nanoparticles' cavity can host a plethora of probes, the device may be modified in order to be specific to certain ROS species, such as hydroxyl, superoxide, nitroxyl, peroxide and other free radicals, while having multimodality through the presence of fluorescent, chemiluminescent, magnetic and X-ray agents. Also, the cerium oxide nanoparticles protect the therapeutic device's fluorophore against UV radiation, hence making the device suitable for clinical applications, such as chemotherapy, and industry-related activities, including, but not limited to prosthesis, post transplant operations, UV protection, chemical synthesis, pharmaceutical research and development, basic and clinical research.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. An implantable device for imaging detection of reactive oxygen species associated with aberrant clinical conditions, comprising a first chamber having an interior cavity including therein a reactive oxygen species (ROS) scavenging component and an exterior semi-permeable membrane encapsulating the ROS scavenging component within the first chamber; said ROS scavenging component being polymeric nanoparticles encapsulating a non-metallic ROS scavenging agent selected from the group consisting of catalase, superoxide dismutase, peroxidase, and glutathione, and said ROS scavenging component capable of scavenging reactive oxygen species under a normal physiological condition;

a second chamber having an interior cavity including therein nanoparticles containing one or more imaging agent and an exterior semi-permeable membrane encapsulating the nanoparticles containing imaging agent within the second chamber; and the first chamber and the second chamber joined in a non-communicating manner, each chamber communicating with an aqueous environment through the semi-permeable membrane thereof, permitting diffusion of the reactive oxygen species therethrough, such that said ROS scavenging component in the first chamber protects the nanoparticles containing imaging agent in the second chamber from the reactive oxygen species under the normal physiological condition; said nanoparticles containing imaging agent in the second chamber incurring an imaging detectable change in the presence of an elevated non-physiological level of the reactive oxygen species in vivo associated with an aberrant clinical condition when scavenging of the reactive oxygen species by the ROS scavenging component is insufficient, thereby indicating the presence of an elevated non-physiological level of the reactive oxygen species.

2. The device of claim 1, wherein the aberrant clinical condition includes inflammation, exposure to radiation, or changes in a tissue/cellular micro-environment.

3. The device of claim 1, wherein the device is a miniature device suitable for in vivo monitoring a potential induction of inflammation during medical treatments.

4. The device of claim 1, wherein the imaging agent comprises at least one of a fluorophore capable of fluorescence emission, a chemiluminescent agent, a magnetic relaxation agent and an X-ray contrast agent.

5. The device of claim 4, wherein the imaging agent is a hydrophobic fluorophore selected from at least one of octodecyl indocarbocyanine(DiI), indodicarbocyanine (DiD), and indotricarbocyanine (DiR).

6. The device of claim 4, wherein the imaging agent is a hydrophobic fluorophore selected from at least one of cyanine 5.5 (Cy5.5) and indocyanine green (ICG).

7. The device of claim 4, wherein the imaging agent is encapsulated in cavities of the nanoparticles in the second chamber.

8. The device of claim 4, wherein the nanoparticles containing imaging agent are nanoparticles of at least one of iron oxide, bismuth, europium, gadolinium and chelates thereof.

9. The device of claim 4, wherein the nanoparticles containing imaging agent are coated with at least one polymer selected from dextran, polyacrylic acid, hyper-branched polyester, poly-lactic-co-glycolic acid, and mixtures thereof.

10. The device of claim 4, wherein the nanoparticles containing imaging agent are polymer-coated nanoparticles of iron oxide for magnetic resonance imaging detection of the reactive oxygen species.

11. The device of claim 4, wherein the nanoparticles containing imaging agent are polymer-coated nanoparticles of iron oxide containing a fluorophore for magnetic resonance imaging and fluorescence imaging detections of the reactive oxygen species.

12. An implantable device for imaging detection of reactive oxygen species associated with aberrant clinical conditions, comprising a first chamber having an interior cavity including therein polymer-coated cerium oxide nanoparticles and an exterior semi-permeable membrane encapsulating the polymer-coated cerium oxide nanoparticles within the first chamber; said polymer-coated cerium oxide nanoparticles capable of scavenging reactive oxygen species under a normal physiological condition;

a second chamber having an interior cavity including therein nanoparticles containing one or more imaging agent and an exterior semi-permeable membrane encapsulating the nanoparticles containing imaging agent within the second chamber; and the first chamber and the second chamber joined in a non-communicating manner, each chamber communicating with an aqueous environment through the semi-permeable membrane thereof, permitting diffusion of the reactive oxygen species therethrough, such that said polymer-coated cerium oxide nanoparticles in the first chamber protects the nanoparticles containing imaging agent in the second chamber from the reactive oxygen species under the normal physiological condition; said nanoparticles containing imaging agent in the second chamber incurring an imaging detectable change in the presence of an elevated non-physiological level of the reactive oxygen species in vivo associated with an aberrant clinical condition when scavenging of the reactive oxygen species by the polymer-coated cerium oxide nanoparticles is insufficient, thereby indicating the presence of an elevated non-physiological level of the reactive oxygen species.

13. The device of claim 12, wherein the polymer-coated cerium oxide nanoparticles are coated with at least one polymer.

14. The device of claim 12, wherein the polymer-coated cerium oxide nanoparticles are coated with dextran or polyacrylic acid.

15. The device of claim 12, wherein the aberrant clinical condition includes inflammation, exposure to radiation, or changes in a tissue/cellular micro-environment.

16. The device of claim 12, wherein the device is a miniature device suitable for in vivo monitoring a potential induction of inflammation during medical treatments.

17. The device of claim 12, wherein the imaging agent comprises at least one of a fluorophore capable of fluorescence emission, a chemiluminescent agent, a magnetic relaxation agent, and an X-ray contrast agent.

18. The device of claim 17, wherein the imaging agent is a hydrophobic fluorophore selected from at least one of octodecyl indocarbocyanine(DiI), indodicarbocyanine (DiD), and indotricarbocyanine (DiR).

19. The device of claim 17, wherein the imaging agent is a hydrophobic fluorophore selected from at least one of cyanine 5.5 (Cy5.5) and indocyanine green (ICG).

20. The device of claim 17, wherein the imaging agent is encapsulated in cavities of the nanoparticles in the second chamber.

21. The device of claim 17, wherein the nanoparticles containing imaging agent are nanoparticles of at least one of iron oxide, bismuth, europium, gadolinium and chelates thereof.

22. The device of claim 17, wherein the nanoparticles containing imaging agent are coated with at least one polymer selected from dextran, polyacrylic acid, hyper-branched polyester, poly-lactic-co-glycolic acid, and mixtures thereof.

23. The device of claim 17, wherein the nanoparticles containing imaging agent are polymer-coated nanoparticles of iron oxide for magnetic resonance imaging detection of the reactive oxygen species.

24. The device of claim 17, wherein the nanoparticles containing imaging agent are polymer-coated nanoparticles of iron oxide containing a fluorophore for magnetic resonance imaging and fluorescence imaging detections of the reactive oxygen species.

* * * * *